(12) United States Patent
Tuck et al.

(10) Patent No.: US 7,223,398 B1
(45) Date of Patent: May 29, 2007

(54) IMMUNOMODULATORY COMPOSITIONS CONTAINING AN IMMUNOSTIMULATORY SEQUENCE LINKED TO ANTIGEN AND METHODS OF USE THEREOF

(75) Inventors: Stephen Tuck, Oakland, CA (US); Gary Van Nest, Martinez, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 09/713,136

(22) Filed: Nov. 14, 2000

Related U.S. Application Data

(60) Provisional application No. 60/165,467, filed on Nov. 15, 1999.

(51) Int. Cl.
*A61K 39/35* (2006.01)
*A61K 39/36* (2006.01)
*A61K 39/385* (2006.01)
*C07H 21/04* (2006.01)

(52) U.S. Cl. .............................. 424/184.1; 424/185.1; 424/193.1; 536/23.1

(58) Field of Classification Search ............. 424/193.1; 514/44
See application file for complete search history.

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,663,153 A | 9/1997 | Hutcherson et al. | |
| 5,723,335 A | 3/1998 | Hutcherson et al. | |
| 5,849,719 A | 12/1998 | Carson et al. | |
| 6,225,292 B1 * | 5/2001 | Raz et al. | |
| 6,498,148 B1 | 12/2002 | Raz | |
| 6,534,062 B2 | 3/2003 | Raz et al. | |
| 6,552,006 B2 | 4/2003 | Raz et al. | |
| 6,613,751 B2 | 9/2003 | Raz et al. | |

FOREIGN PATENT DOCUMENTS

| | | |
|---|---|---|
| EP | 0 468 520 A2 | 1/1992 |
| WO | WO 96/02555 A1 | 2/1996 |
| WO | WO 97/28259 A1 | 8/1997 |
| WO | WO 98/16247 A1 | 4/1998 |
| WO | WO 98/18810 A1 | 5/1998 |
| WO | WO 98/37919 A1 | 9/1998 |
| WO | WO 98/40100 A1 | 9/1998 |
| WO | WO 98/52581 A1 | 11/1998 |
| WO | WO 98/52962 A1 | 11/1998 |
| WO | WO 98/55495 A2 | 12/1998 |
| WO | WO 98/55495 A3 | 12/1998 |
| WO | WO 98/55609 A1 | 12/1998 |
| WO | WO 99/11275 A2 | 3/1999 |
| WO | WO 99/11275 A3 | 3/1999 |
| WO | WO 99/33488 A2 | 7/1999 |
| WO | WO 99/33488 A3 | 7/1999 |
| WO | WO 99/33868 A2 | 7/1999 |
| WO | WO 99/33868 A3 | 7/1999 |
| WO | WO 99/51259 A2 | 10/1999 |
| WO | WO 99/56755 A1 | 11/1999 |
| WO | WO 99/62923 A2 | 12/1999 |

OTHER PUBLICATIONS

Hirschwehr et al J Allergy Clin Immunol 101: 196-206, 1995.*
Ngo et al, in The Protein Folding Problem and Tertiary Structure Prediction, pp. 492-495, 1994.*
Stryer et al, in Biochemistry, W.H. Freeman and COmpany, New York, pp. 31-33, 1988.*
Yamada et al, J Immunology 169: 5590-5594, 2002.*
Segal et al, J Immunology 164: 5683-88, 2000.*
Chatel et al, Allergey 58: 641-647, 2003.*
Klinman et al, Vaccine 17: 19-25, Jan. 1999.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Agrawal et al. (1986). "Efficient methods for attaching non-radio-active labels to the 5' ends of synthetic oligodeoxyribonucleotides," *Nucleic Acids Res.* 14:6227-6245.
Ahmeida et al. (1993). "Immunopotentiation of local and systemic humoral immune responses by ISCOMs, liposomes and FCA: role in protection against influenza A in mice," *Vaccine* 11(13):1302-1309.
Aramaki et al. (1995). "Interferon -γ inductive effect of liposomes as an immunoadjuvant," *Vaccine* 13(18):1809-1814.
Asanuma et al. (1996). "Cross-protection against influenza virus infection in mice vaccinated by combined nasal/subcutaneous administration," *Vaccine* 13(1):3-5.
Atherton et al. (1981). "Synthesis of a 21-residue fragment of human proinsulin by the polyamide solid phase method," *Hoppe-Seylers Z. Physiol. Chem.* 362:833-839.

(Continued)

*Primary Examiner*—Christina Chan
*Assistant Examiner*—Phuong Huynh
(74) *Attorney, Agent, or Firm*—Morrison & Foerster LLP

(57) ABSTRACT

The invention provides classes of immunomodulatory compositions which comprise an average of one or more immunostimulatory sequence (ISS) containing polynucleotide conjugated, or attached, to antigen. The extent of conjugation affects immunomodulatory properties, such as extent of antigen-specific antibody formation, including Th1-associated antibody formation, and thus these various conjugate classes are useful for modulating the type and extent of immune response. The invention also includes methods of modulating an immune response using these compositions.

31 Claims, 16 Drawing Sheets

OTHER PUBLICATIONS

Ballas et al. (1996). "Induction of NK activity in murine and human cells by CpG motifs in oligodeoxynucleotides and bacterial DNA," *J.Immunol.* 157:1840-1845.

Beaucage, Serge L. (1993). "Oligodeoxyribonucleotides synthesis," Chapter 3 in *Methods in Molecular Biology: Protocols for Oligonucleotides and Analogs* vol. 20, Agrawal, Sudhir, ed. Humana Press: pp. 33-61.

Benoit et al. (1987). "Peptides. Strategies for antibody production and radioimmunoassays," *Neuromethods* 6:43-72.

Bischoff et al. (1987). "Introduction of 5'-terminal functional groups into synthetic oligonucleotides for selective immobilization," *Analytical Biochemistry* 164:336-344.

Blanks, Robert and McLaughlin, Larry W. (1988). "An oligodeoxynucleotide affinity column for the isolation of sequence specific DNA binding proteins," *Nucleic Acids Res.* 16(21):10283-10299.

Bliss et al. (1996). "IL-12, as an adjuvant, promotes a T helper 1 cell, but does not supress a T helper 2 cell recall response," *J. Immunol.* 156:887-894.

Bohle et al. (1999). "Oligodeoxynucleotides containing CpG motifs induce IL-12, IL-18, and IFN-γ production in cells from allergic individuals and inhibit IgE synthesis in vitro," *Eur. J. Immunol.* 29:2344-2353.

Boujrad et al. (1993). "Inhibition of hormone-stimulated steroidogenesis in cultured Leydig tumor cells by a cholestrol-linked phosphorothioate oligodeoxynucleotide antisense to diazepam-binding inhibitor," *Proc. Natl. Acad. Sci. USA* 90:5728-5731.

Branda et al. (1993). "Immune stimulation by an antisense oligomer complementary to the rev gene of HIV-1," *Biochem. Pharmacol.* 45(10):2037-2043.

Branda et al. (1996). "Amplification of antibody production by phosphorothioate oligodeoxynucleotides," *J. Lab. Clin. Med.* 128(3):329-338.

Braun et al. (1988). "Immunogenic duplex nucleic acids are nuclease resistant," *J. Immunol.* 141:2084-2089.

Brazolot Millan et al. (1998) "CpG DNA can induce strong Th1 humoral and cell-mediated immune responses against hepatitis B surface antigen in young mice," *Proc. Natl. Acad. Sci. USA* 95:15553-15558.

Breiteneder et al. (1989). "The gene coding for the major birch pollen allergen Betv1 is highly homologous to a pea disease resistance response gene," *EMBO J.* 8(7):1935-1938.

Broide et al. (1998). "Immunostimulatory DNA sequences inhibit IL-5, eosinophilic inflammation, and airway hyperresponsiveness in mice," *J. Immunol.* 161:7054-7062.

Broide and Raz (1999). "DNA-based immunization for asthma," *Int. Arch. Allergy Immunol.* 118:453-456.

Carson and Raz (1997). "Oligonucleotide adjuvants for T helper 1 (Th1)-specific vaccination," *J. Exp. Med.* 186(10):1621-1622.

Chace et al. (1997). "Bacterial DNA-induced NK cell IFN-γ production is dependent on macrophage secretion of IL-12," *Clin. Immunol. and Immunopathol.* 84(2):185-193.

Chaturvedi et al. (1996). "Stabilization of triple-stranded oligonucleotide complexes: use of probes containing alternating phosphodiester and stereo-uniform cationic phosphoramidate linkages," *Nucleic Acids Res.* 24(12):2318-2323.

Chen et al. (1999). "Enhanced protection against a lethal influenza virus challenge by immunization with both hemagglutinin- and neuraminidase-expressing DNAs," *Vaccine* 17:653-659.

Chu et al. (1997). "CpG oligodeoxynucleotides act as adjuvants that switch on T helper 1 (Th1) immunity," *J. Exp. Med.* 186(10):1623-1631.

Chua et al. (1988). "Sequence analysis of cDNA coding for a major house dust mite allergen, *Der p 1* homology with cysteine proteases," *J. Exp. Med.* 167:175-182.

Chua et al. (1990). "Expression of *Dermatophagoides pteronyssinus* allergen, *Der p* II, in *Escherichia coli* and the binding studies with human IgE," *Int. Arch. Allergy Appl. Immunol.* 91:124-129.

Connolly, Bernard A. (1985). "Chemical synthesis of oligonucleotides containing a free sulphydryl group and subsequent attachment of thiol specific probes," *Nucleic Acids Res.* 13(12):4485-4502.

Connolly, Bernard A. (1987). "The synthesis of oligonucleotides containing a primary amino group at the 5'-terminus," *Nucleic Acids Res.* 15(7):3131-3139.

Corey et al. (1987). "Generation of a hybrid sequence-specific single-stranded deoxyribonuclease," *Science* 238:1401-1403.

Cowdery et al. (1996). "Bacterial DNA induces NK cells to produce IFN-γ in vivo and increases the toxicity of lipopolysaccharides," *J. Immunol.* 156:4570-4575.

de Martino et al. (1999). "Low IgG3 and high IgG4 subclass levels in children with advanced human immunodeficiency virus-type 1 infection and elevated IgE levels," *Ann. Allergy Asthma Immunol.* 83:160-164.

Elkins et al. (1999). "Bacterial DNA containing CpG motifs stimulates lymphocyte-dependent protection of mice against lethal infection with intracellular bacteria" *J. Immunol.* 162:2291-2298.

Elsayed et al. (1991). "The structural requirements of epitopes with IgE binding capacity demonstrated by three major allergens from fish, egg and tree pollen," *Scand. J. Clin. Lab. Invest. Suppl.* 51(Suppl. 204):17-31.

Fornadley, John (1998). "Allergy immunotherapy," *Otolaryngol. Clin. North Am.* 31(1):111-127.

Gao et al., (1995). "Circularization of oligonucleotides by disulfide bridge formation," *Nucleic Acids Res.* 23(11):2025-2029.

Geoghegan and Stroh (1992). "Site-directed conjugation of nonpeptide groups to peptides and proteins via periodate oxidation of a 2-amino alcohol. Application to modification at N-terminal serine," *Bioconjug. Chem.* 3(2):138-146.

Goodchild, John (1990). "Conjugates of oligonucleotides and modified oligonucleotides: A review of their synthesis and properties" *Bioconjug. Chem.* 1(3):165-187.

Govorkova and Smirnov (1997). "Cross-protection of mice immunized with different influenza A (H2) strains and challenged with viruses of the same HA subtype" *Acta Virologica* 41:251-257.

Grabarek et al. (1990). "Zero-length corsslinking procedure with the use of active esters" *Anal. Biochem.* 185:131-135.

Gramzinski et al. (1998). "Immune response to a hepatitis B DNA vaccine in *aotus* monkeys: A comparison of vaccine formulation, route, and method of administration," *Mol. Med.* 4:109-118.

Granoff, Dan M. (1993). "Effect of immunity to the carrier protein on antibody responses to *Haemophilus influenzae* type b conjugate vaccines," *Vaccine* 11(Suppl.1):S46-S51.

Haralambidis et al. (1990). "The preparation of polyamide-oligonucleotide probes containing multiple non-radioactive labels," *Nucleic Acids Res.* 18:501-505.

Haralambidis et al. (1990). "The synthesis of polyamide-oligonucleotide conjugate molecules," *Nucleic Acids Res.* 18(3):493-499.

Horner et al. (1998). "Rapid communication: Immunostimulatory DNA is a potent mucosal adjuvant," *Cell Immunol.* 190:77-82.

Jäger et al. (1988). "Oligonucleotide N-alkylphosphoramidates: Synthesis and binding to polynucleotides," *Biochem.* 27:7237-7246.

Jakob et al. (1998). "Activation of cutaneous dendrific cells by CpG-containing oligodeoxynucleotides: A role for dendritic cells in the augmentation of Th1 responses by immunostimulatory DNA," *J. Immunol.* 161:3042-3049.

Kataoka et al. (1992). "Antitumor activity of synthetic oligonucleotides with sequences from cDNA encoding proteins of *mycobacterium bovis* BCG," *Jpn. J. Cancer Res.* 83:244-247.

Kessler, Christoph (1992). "Nonradioactive labeling methods for nucleic acids," in *Nonisotopic DNA Probe Techniques.* Kricka ed. Academic Press, Inc.: pp. 29-92.

Kikuta et al. (1990). "Cross-protection against influenza B type virus infection by intranasal inoculation of the HA vaccines combined with cholera toxin B subunit," *Vaccine* 8(6):595-599.

Kimura et al. (1994). "Binding of oligoguanylate to scavenger receptors is required for oligonucleotides to augment NK cell activity and induce IFN," *J. Biochem. (Tokyo)* 116:991-994.

Kline et al. (1997). "Immune redirection by CpG oligonucleotides conversion of a Th2 response to a Th1 response in a murine model of asthma," *J. Invest. Med.* 45(3):282A.

Klinman et al. (1996). "CpG motifs present in bacterial DNA rapidly induce lymphocytes to secrete interleukin 6, interleukin 12, and interferon γ," *Proc. Natl. Acad. Sci. USA* 93:2879-2883.

Klinman et al., (1997). "Contribution of CpG motifs to the immunogenicity of DNA vaccines," *J. Immunol.* 158:3635-3639.

Kodihalli et al. (1997). "Cross-protection among lethal H5N2 influenza viruses induced by DNA vaccine to the hemagglutinin," *J. Virol.* 71(5):3391-3396.

Kovarik et al. (1999). "CpG oligodeoxynucleotides can circumvent the Th2 polarization of neonatal responses to vaccines but may fail to fully redirect Th2 responses established by neonatal priming," *J. Immunol.* 162:1611-1617.

Kremsky et al. (1987). "Immunobilization of DNA via oligonucleotides containing an aldehyde or carboxylic acid group at the 5' terminus," *Nucleic Acids Res.* 15(7):2891-2909.

Krieg et al. (1989). "A role for endogenous retroviral sequences in the regulation of lymphocyte activation," *J. Immunol.* 143(8):2448-2451.

Krieg et al. (1995). "CpG motifs in bacterial DNA trigger direct B-cell activation" *Nature* 374:546-549.

Krieg et al. (1996). "Oligodeoxynucleotide modifications determine the magnitude of B cell stimulation by CpG motifs," *Antisense & Nucleic Acid Drug Dev.* 6:133-139.

Krieg, Arthur M. (1996). "Lymphocyte activation by CpG dinucleotide motifs in prokaryotic DNA," *Trends in Microbiology* 4(2):73-77.

Krieg, Arthur M. (1998). "Leukocyte stimulation by oligodeoxynucleotides" Chapter 24 in *Applied Antisense Oligonucleotide Technology.* C.A. Stein et al. eds. Wiley-Liss, Inc.: pp. 431-448.

Krieg et al., (1998). "The role of CpG dinucleotides in DNA vaccines," *Trends Microbiol.* 6(1):23-27.

Krieg et al. (1998). "CpG DNA induces sustained IL-12 expression in vivo and resistance to *Listeria monocytogenes* challenge," *J. Immunol.* 161:2428-2434.

Krieg et al. (1998). "Sequence motifs in adenoviral DNA block immune activation by stimulatory CpG motifs," *Proc. Natl. Acad. Sci. USA* 95:12631-12636.

Krieg, Arthur M. (1999). "CpG DNA: a novel immunomodulator," *Trends Microbiol.* 7(2):64-65.

Latimer et al. (1995). "Specificity of monoclonal antibodies produced against phosphorothioate and ribo modified DNAs," *Mol. Immunol.* 32(14/15):1057-1064.

Lea et al. (1996). "Cloning and sequencing of cDNAs encoding the human sperm protein, Sp17," *Biochim. Biophys. Acta* 1307:263-266.

Leclerc et al. (1997). "The preferential induction of a TH1 immune repsonse by DNA-based immunization is mediated by the immunostimulatory effect of plasmid DNA," *Cell. Immunol.* 179:97-106.

Leff, David N. (1997). "Non-lipid polymer beats liposome vector in mouse gene therapy experiment," *BioWorld Today* 86(8):1-2.

Liang et al. (1996). "Activation of human B cells by phosphorothioate oligodeoxynucleotides," *J. Clin. Invest.* 98(5):1119-1129.

Lipford et al. (1997). "CpG-containing synthetic oligonucleotides promote B and cytotoxic T cell responses to protein antigen: a new class of vaccine adjuvants," *Eur. J. Immunol.* 27:2340-2344.

Lipford et al. (1997). "Immunostimulatory DNA: sequence-dependent production of potentially harmful or useful cytokines," *Eur. J. Immunol.* 27:3420-3426.

Liu et al. (1998). "Immunostimulatory CpG oligodeoxynucleotides enhance the immune repsonse to vaccine strategies involving granulocyte-macrophage colony-stimulating factor," *Blood* 92(10):3730-3736.

Macfarlane et al. (1997). "Unmethylated CpG-containing oligodeoxynucleotides inhibit apoptosis in WEHI 231 B lymphocytes induced by several agents: evidence for blockade of apoptosis at a distal signalling step," *Immunology* 91:586-593.

Mahato et al. (1997). "Cationic lipid-based gene delivery systems: Pharmaceutical perspectives" *Pharmaceutical Res.* 14(7):853-859.

Malley, Arthur (1989). "The immune response of offspring mice from mothers immunized during pregnancy with protein antigens," *J Reprod. Immunol.* 16:173-186.

Martin-Orozco et al. (1999). "Enhancement of antigen-presenting cell surface molecules involved in cognate interactions by immunostimulatory DNA sequences," *Intnl Immunol.* 11(7):1111-1118.

Matteucci, Mark (1997). "Oligonucleotide analogues: an overview," *CIBA Foundation Symposium 209: Oligonucleotides as Therapeutic Agents*, pp. 5-18.

Mbawuike et al. (1994). "Influenza: A subtype cross-protection after immunization of outbred mice with a purified chimeric $NS_1/HA_2$ influenza virus protein," *Vaccine* 12(14):1340-1348.

McCluskie et al. (1998). "Cutting edge: CpG DNA is a potent enhancer of systemic and mucosal immune responses against hepatitis B surface antigen with intranasal administration to mice," *J. Immunol.* 161(9):4463-4466.

Miller et al. (1971). "Syntheses and properties of adenine and thymine nucleoside alkyl phosphotriesters, the neutral analogs of dinucleoside monophosphates," *JACS* 93:6657-6665.

Mitragotri et al. (1995). "Ultrasound-mediated transdermal protein delivery," *Science* 269:850-853.

Mojcik et al. (1993). "Administration of a phosphorothioate oligonucleotide antisense to murine endogenous retroviral MCF *env* causes immune effects in vivo in a sequence-specific manner," *Clin. Immuno. and Immunopathol.* 67(2):130-136.

Moldoveanu et al. (1998). "CpG DNA, a novel immune enhancer for systemic and mucosal immunization with influenza virus," *Vaccine* 16(11/12):1216-1224.

Nelson et al. (1989). "Bifunctional oligonucleotide probes synthesized using a novel CPG support are able to detect single base pair mutations," *Nucleic Acids Res.* 17(18):7187-7194.

Nelson et al. (1997). "N3'→P5' oligodeoxyribonucleotide phosphoramidates: A new method of synthesis based on a phosphoramidite amino-exchange reaction," *J. Org. Chem.* 62:7278-7287.

O'Shannessy and Quarles (1985). "Specific conjugation reactions of the oligosaccharide moieties of immunoglobulins," *J. Applied Biochem.* 7:347-355.

Pertmer et al. (1996). "Influenza virus nucleoprotein-specific immunoglobulin G subclass and cytokine responses elicited by DNA vaccination are dependent on the route of vector DNA delivery," *J. Virol.* 70(9):6119-6125.

Peyrottes et al. (1996). "Oligodeoxynucleoside phosphoramidates ($P-NH_2$): synthesis and thermal stability of duplexes with DNA and RNA targets," *Nucleic Acids Res.* 24(10):1841-1848.

Pisetsky and Reich (1994). "Stimulation of murine lymphocyte proliferation by a phosphorothioate oligonucleotide with antisense activity for herpes simplex virus," *Life Sci.* 54:101-107.

Pisetsky et al. (1995). "Immunological properties of bacterial DNA," in *DNA Vaccines: A New Era in Vaccinology.* Liu et al. eds. Ann. N.Y. Acad. Sci.:772:152-163.

Pisetsky, David S. (1996). "The immunologic properties of DNA," *J. Immunol.* 156(2):421-423.

Pisetsky, David S. (1996). "Immune activation by bacterial DNA: A new genetic code," *Immunity* 5:303-310.

Rafnar et al. (1991). "Cloning of *Amb a I* (antigen E), the major allergen family of short ragweed pollen," *J. Biol. Chem.* 266(2):1229-1236.

Raz et al. (1994). "Intradermal gene immunization: The possible role of DNA uptake in the induction of cellular immunity to viruses," *Proc. Natl. Acad. Sci. USA* 91:9519-9523.

Raz et al. (1996) "Preferential induction of a $Th_1$ immune response and inhibition of specific IgE antibody formation by plasmid DNA immunization," *Proc. Natl. Acad. Sci. USA* 93:5141-5145.

Redford et al. (1998). "Cyclosporin A enhances IL-12 production by CpG motifs in bacterial DNA and synthetic oligodeoxynucleotides," *J. Immunol.* 161:3930-3935.

Rogers et al. (1993). "Recombinant *Fel d I*: Expression, purification, IgE binding and reaction with cat-allergic human T cells," *Mol. Immunol.* 30(6):559-568.

Roget et al. (1989). "Synthesis and use of labelled nucleoside phosphoramidite building blocks bearing a reporter group: biotinyl, dinitrophenyl, pyrenyl and dansyl," *Nucleic Acids Res.* 17(19):7643-7651.

Roman et al. (1997). "Immunostimulatory DNA sequences function as T helper-1-promoting adjuvants," *Nature Medicine* 3(8):849-854.

Ruth, Jerry L. (1991). "Oligodeoxynucleotides with reporter groups attached to the base" in *Oligonucleotides and Analogues: A Practical Approach*. Eckstein, ed. IRL Press: pp. 255-282.

Sato et al. (1996). "Immunostimulatory DNA sequences necessary for effective intradermal gene immunization," *Science* 273:352-354.

Scherle et al. (1986). "Functional analysis of influenza speicific helper T cell clones in vivo," *J. Exp. Med.* 164:1114-1128.

Scherle et al. (1988). "Differential ability of B cells specific for external vs. internal influenza virus proteins to respond to help from influenza virus-specific T-cell clones in vivo," *Proc. Natl. Acad. Sci. USA* 85:4446-4450.

Schultz and Gryaznov (1996) "Oligo-2'-fluoro-2'-deoxynucleotide N3'→P5' phosphoramidates: synthesis and properties," *Nucleic Acids Res.* 24(15):2966-2973.

Schwartz et al. (1997). "CpG motifs in bacterial DNA cause inflammation in the lower respiratory tract," *J. Clin. Invest.* 100(1):68-73.

Shimada et al. (1986). "In vivo augmentation of natural killer cell activity with a deoxyribonucleic acid fraction of BCG," *Jpn. J. Cancer Res.* 77:808-816.

Sinha et al. (1991). "Oligonucleotides with reporter groups attached to the 5'-terminus" in *Oligonucleotide and Analogues: A Practical Approach*. Eckstein, ed. IRL Press: pp. 185-210.

Sonehara et al. (1996). "Hexamer palindromic oligonucleotides with 5'-CG-3' motif(s) induce production of interferon," *J. Interferon and Cytokine Res.* 16:799-803.

Sparwasser et al. (1997). "Macrophages sense pathogens via DNA motifs: induction of tumor necrosis factor-α-mediated shock," *Eur. J. Immunol.* 27:1671-1679.

Spiegelberg et al. (1998). "Inhibition of IgE formation and allergic inflammation by allergen gene immunization and by CpG motif immunostimulatory oligodeoxynucleotides," *Allergy* 53:93-97.

Spiegelberg et al. (1999). "Inhibition of allergic inflammation in the lung by plasmid DNA allergen immunization," *Pediatric Pulmonary* Supplement 18:118-121.

Stacey et al. (1996). "Macrophage ingest and are activated by bacterial DNA," *J. Immunol.* 157:2116-2122.

Staros et al. (1986). "Enhancement by N-hydroxysulfosuccinimide of water-soluble carbodiimide-mediated coupling reactions," *Anal. Biochem.* 156:220-222.

Stein and Kreig (1997). "Non-antisense effects of oligodeoxynucleotides," Chapter 11 in *Antisense Technology*. Lichtenstein and Nellen, eds. IRL Press: pp. 241-264.

Stirchak et al. (1989). "Uncharged stereoregular nucleic acid analogs: 2. Morpholino nucleoside oligomers with carbamate internucleoside linkages," *Nucleic Acids Res.* 17(15):6129-6141.

Takahashi et al. (1990). "Induction of CD8+cytotoxic T cells by immunization with purified HIV-1 envelope protein in ISCOMs," *Nature* 344:873-875.

Tamura et al. (1992). "Superior cross-protective effect of nasal vaccination to subcutaneous inoculation with influenza hemagglutinin vaccine," *Eur. J. Immunol.* 22:477-481.

Tamura et al. (1994). "Formulation of inactivated influenza vaccines for providing effective cross-protection by intranasal vaccination in mice," *Vaccine* 12(4):310-316.

"The Human Retroviruses and AIDS 1998 Compendium" pp. 1-3 (Contents Part I, I-1, II-4), "Direct Submission" at http://hiv-web.lanl.gov/HTML/98compendium.html (visited on Feb. 1, 2000).

Tighe et al. (2000). "Conjugation of immunostimulatory DNA to the short ragweed allergen Amb a 1 enhances its immunogenicity and reduces its allergenicity," *J. Allergy Clin. Immunol.* 106(1):124-134.

Tokunaga et al. (1992). "Synthetic oligonucleotides with particular base sequences from the cDNA encoding proteins of Mycobacterium bovis BCG induce interferons and activate natural killer cells," *Microbiol. Immunol.* 36(1):55-66.

Tung et al. (1991). "Preparation of oligonucleotide-peptide conjugates," *Bioconjug. Chem.* 2:464-465.

Van Uden and Raz (1999). "Immunostimulatory DNA and applications to allergic disease," *J. Allergy Clin. Immunol.* 104(5):902-910.

Wang and Kool (1994). "Circular RNA oligonucleotides. Synthesis, nucleic acid binding properties, and a comparison with circular DNAs," (1994) *Nucleic Acids Res.* 22(12):2326-2333.

Warner et al. (1984). "Laboratory methods. Construction and evaluation of an instrument for the automated synthesis of oligodeoxyribonucleotides," *DNA* 3(5):401-411.

Watwe and Bellare (1995). "Manufacture of liposomes: A review," *Curr. Sci.* 68(7):715-724.

Weeratna et al. (1998). "Reduction of antigen expression from DNA vaccines by coadministered oligodeoxynucleotides" *Antisense & Nucleic Acid Drug Dev.* 8:351-356.

Weiner et al. (1997). "Immunostimulatory oligodeoxynucleotides containing the CpG motif are effective as immune adjuvants in tumor antigen immunization," *Proc. Natl. Acad. Sci. USA* 94:10833-10837.

Widhe et al. (1998). "IgG subclasses in lyme borreliosis: A study of specific IgG subclass distribution in an interferon-γ-predominated disease," *Scand. J. Immunol.* 47:575-581.

Wooldridge et al. (1997). "Immunostimulatory oligodeoxynucleotides containing CpG motifs enhance the efficacy of monoclonal antibody therapy of lymphoma," *Blood* 89(8):2994-2998.

Yamamoto et al. (1992). "Unique palindromic sequences in synthetic oligonucleotides are required to induce INF and augment INF-mediated natural killer activity," *J. Immunol.* 148(12):4072-4076.

Yamamoto et al. (1992). "DNA from bacteria, but not from vertebrates, induces interferons, activates natural killer cells and inhibits tumor growth," *Microbiol. Immunol.* 36(9):983-997.

Yamamoto et al. (1994). "Ability of oligonucleotides with certain palindromes to induce interferon production and augment natural killer cell activity is associated with their base length," *Antisense Research and Development*. 4:119-122.

Yamamoto et al. (1994). "Synthetic oligonucleotides with certain palindromes stimulate interferon production of human peripheral blood lymphocytes in vitro," *Jpn. J. Cancer Res.* 85:775-779.

Yanagawa et al. (1988). "Analysis of superhelical structures of nucleic acid—lipid conjugates by image processing," *Nucleic Acids Symp. Series* 19:189-192.

Yi et al. (1996). "IFN-γ promotes IL-6 and IgM secretion in response to CpG motifs in bacterial DNA and oligodeoxynucleotides," *J. Immunol.* 156:558-564.

Yi and Krieg (1998). "CpG DNA rescue from anti-IgM-induced WEHI-231 B lymphoma apoptosis via modulation of IκBα and IκBβ and sustained activation of nuclear factor-κB/c-Rel," *J. Immunol.* 160(3):1240-1245.

Yi et al. (1998). "CpG motifs in bacterial DNA activate leukocytes through the pH-dependent generation of reactive oxygen species," *J. Immunol.* 160(10):4755-4761.

Yi et al. (1998). "CpG oligodeoxynucleotides rescue mature spleen B cells from spontaneous apoptosis and promote cell cycle entry," *J. Immunol.* 160(12):5898-5906.

.Yi and Krieg (1998). "Cutting edge: Rapid induction of mitogen-activated protein kinases by immune stimulatory CpG DNA," *J. Immunol.* 161(9):4493-4497.

Zhao et al. (1996). "Effect of different chemically modified oligodeoxynucleotides on immune stimulation" *Biochem. Pharmacol.* 51:173-182.

Zimmerman et al. (1998). "Cutting edge: CpG oligodeoxynucleotides trigger protective and curative Th1 responses in lethal murine leishmaniasis," *J. Immunol.* 160(8):3627-3630.

Zon, Gerald, (1993). "Oligonucleoside phosphorothioates," Chapter 8 in *Methods in Molecular Biology: Protocols for Oligonucleotides and Analogs* vol. 20, Agrawal, Sudhir, ed. Humana Press: pp. 165-189.

Zuckermann et al. (1987). "Efficient methods for attachment of thiol specific probes to the 3'-ends of synthetic oligodeoxyribonucleotides," *Nucleic Acids Res.* 15(13):5305-5321.

* cited by examiner

SEQUENCE LISTING

<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: synthetic construct

<400> SEQUENCE: 1
tgactgtgaa cgttcgagat ga 22

<210> SEQ ID NO 2
<211> LENGTH: 22
<212> TYPE: DNA
<213> ORGANISM: Artificial Sequence
<220> FEATURE:
<223> OTHER INFORMATION: synthetic construct

<400> SEQUENCE: 2
tgaccgtgaa cgttcgagat ga 22

<210> SEQ ID NO 3
<211> LENGTH: 23
<212> TYPE: DNA
<213> ORGANISM: Artificial Sequence
<220> FEATURE:
<223> OTHER INFORMATION: synthetic construct

<400> SEQUENCE: 3
tcatctcgaa cgttccacag tca 23

<210> SEQ ID NO 4
<211> LENGTH: 22
<212> TYPE: DNA
<213> ORGANISM: Artificial Sequence
<220> FEATURE:
<223> OTHER INFORMATION: synthetic construct

<400> SEQUENCE: 4

```
tgactgtgaa cgttccagat ga                                              22

<210> SEQ ID NO 5
<211> LENGTH: 26
<212> TYPE: DNA
<213> ORGANISM: Artificial Sequence
<220> FEATURE:
<223> OTHER INFORMATION: synthetic construct

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial Sequence
<220> FEATURE:
<223> OTHER INFORMATION: synthetic construct
<221> NAME/KEY: modified_base
<222> LOCATION: (11)...(0)
<223> OTHER INFORMATION: N = 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: synthetic construct
<221> NAME/KEY: modified_base
<222> LOCATION: (11)...(0)
<223> OTHER INFORMATION: N = 5-bromocytosine

<400> SEQUENCE: 7
tgactgtgaa ngttcgagat ga                                              22

<210> SEQ ID NO 8
<211> LENGTH: 22
<212> TYPE: DNA
<213> ORGANISM: Artificial Sequence
<220> FEATURE:
<223> OTHER INFORMATION: synthetic construct
<221> NAME/KEY: modified_base
<222> LOCATION: (11)...(0)
<223> OTHER INFORMATION: N = 5-bromocytosine

<400> SEQUENCE: 8
tgactgtgaa ngttbgagat ga                                              22

<210> SEQ ID NO 9
<211> LENGTH: 22
<212> TYPE: DNA
<213> ORGANISM: Artificial Sequence
<220> FEATURE:
<223> OTHER INFORMATION: synthetic construct

<400> SEQUENCE: 9
tgactgtgaa ggttagagat ga                                              22

<210> SEQ ID NO 10
<211> LENGTH: 22
<212> TYPE: DNA
<213> ORGANISM: Artificial Sequence
<220> FEATURE:
<223> OTHER INFORMATION: synthetic construct
```

```
<400> SEQUENCE: 10
tgactgtgaa ccttagagat ga                                              22

<210> SEQ ID NO 11
<211> LENGTH: 8
<212> TYPE: PRT
<213> ORGANISM: Artificial Sequence
<220> FEATURE:
<223> OTHER INFORMATION: synthetic construct

<400> SEQUENCE: 11

Ser Ile Ile Asn Phe Glu Lys Leu
 1               5
```

IMMUNOMODULATORY COMPOSITIONS CONTAINING AN IMMUNOSTIMULATORY SEQUENCE LINKED TO ANTIGEN AND METHODS OF USE THEREOF

CROSS-REFERENCE TO RELATED APPLICATIONS

This application claims the priority benefit of U.S. Provisional application 60/165,467, filed Nov. 15, 1999, which is hereby incorporated herein by reference in its entirety.

TECHNICAL FIELD

This invention relates to the field of immunology, more particularly use of immunostimulatory polynucleotide sequences attached to antigen to modulate an immune response.

BACKGROUND ART

Immune responses to resolve different pathologies, such as those seen in viral infections, bacterial infections, cancer, and allergic reactions are important to the overall health of the host. Successful resolution of infections, cancer, or allergic reactions may depend on the type and magnitude of the immune response. Immunizations, whereby antigen is used to elicit further immune responses, may be helpful in the successfully resolving the infections, cancers, and/or allergic reactions. Since the type of antigen used to elicit immune response is different from one disease to the next, it would be desirable to have a method of immunization that would enable the immune system to address all the aforementioned infections and diseases. More specifically, it would be desirable to have a method of immunization that enabled differential modulation of immune responses. While immunizations, in general, have tended to induce humoral (antibody) responses, it may be preferable to induce another type of immune response, namely, cellular immune response to avoid complications that may arise from a humoral response (e.g., anaphylactic shock).

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct pattern of cytokines that negatively regulate each other. For example, IL-2 shifts the immune response toward Th1 and inhibits the development of Th2 response. Likewise, IL-10, another Th2 cytokine, shifts the immune response towards Th2 and inhibits the development of Th1 response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849–854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66–75%. Raz et al. (1996) *Proc. Natl. Acad. Sci. USA* 93:5141–5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

It has been reported that linking ISS to antigen results in a significant enhancement of the Th1 immune response compared to co-administration of ISS and antigen in an admixture. See, for example, WO 98/16247; WO 98/55495.

Other references describing ISS include: Krieg et al. (1989) *J. Immunol.* 143:2448–2451; Tokunaga et al. (1992) *Microbiol. Immunol.* 36:55–66; Kataoka et al. (1992) *Jpn. J. Cancer Res.* 83:244–247; Yamamoto et al. (1992a) *J. Immunol.* 148:4072–4076; Yamamoto et al. (1992b) *Microbiol. Immunol.* 36:983–997; Mojcik et al. (1993) *Clin. Immuno. and Immunopathol.* 67:130–136; Branda et al. (1993) *Biochem. Pharmacol.* 45:2037–2043; Pisetsky et al. (1994) *Life Sci.* 54(2):101–107; Yamamoto et al. (1994a) *Antisense Research and Development.* 4:119–122; Yamamoto et al. (1994b) *Jpn. J. Cancer Res.* 85:775–779; Raz et al. (1994) *Proc. Natl. Acad. Sci. USA* 91:9519–9523; Kimura et al. (1994) *J. Biochem.* (Tokyo) 116:991–994; Krieg et al. (1995) *Nature* 374:546–549; Pisetsky et al. (1995) *Ann. N.Y. Acad. Sci.* 772:152–163; Pisetsky (1996a) *J. Immunol.* 156: 421-423; Pisetsky (1996b) *Immunity* 5:303–310; Zhao et al. (1996) *Biochem. Pharmacol.* 51:173–182; Yi et al. (1996) *J. Immunol.* 156:558–564; Krieg (1996) *Trends Microbiol.* 4(2):73–76; Krieg et al. (1996) *Antisense Nucleic Acid Drug Dev.* 6:133–139; Klinman et al. (1996) *Proc. Natl. Acad. Sci. USA* 93:2879–2883; Raz et al. (1996); Sato et al. (1996) *Science* 273:352–354; Stacey et al. (1996) *J. Immunol.* 157:2116–2122; Ballas et al. (1996) *J. Immunol.* 157:1840–1845; Branda et al. (1996) *J. Lab. Clin. Med.* 128:329–338; Sonehara et al. (1996) *J. Interferon and Cytokine Res.* 16:799–803; Klinman et al. (1997) *J. Immunol.* 158:3635–3639; Sparwasser et al. (1997) *Eur. J. Immunol.* 27:1671–1679; Roman et al. (1997); Carson et al. (1997) *J. Exp. Med.* 186:1621–1622; Chace et al. (1997) *Clin. Immunol. and Immunopathol.* 84:185–193; Chu et al. (1997) *J. Exp. Med.* 186:1623–1631; Lipford et al. (1997a) *Eur. J. Immunol.* 27:2340–2344; Lipford et al. (1997b) *Eur. J. Immunol.* 27:3420–3426; Weiner et al. (1997) *Proc. Natl. Acad. Sci. USA* 94:10833–10837; Macfarlane et al. (1997) *Immunology* 91:586–593; Schwartz et al. (1997) *J. Clin. Invest.* 100:68–73; Stein et al. (1997) *Antisense Technology*, Ch. 11 pp. 241–264, C. Lichtenstein and W. Nellen, Eds., IRL Press; Wooldridge et al. (1997) *Blood* 89:2994–2998; Leclerc et al. (1997) *Cell. Immunol.* 179:97–106; Kline et al. (1997) *J. Invest. Med.* 45(3):282A; Yi et al. (1998a) *J. Immunol.* 160:1240–1245; Yi et al. (1998b) *J. Immunol.* 160:4755–4761; Yi et al. (1998c) *J. Immunol.* 160:5898–5906; Yi et al. (1998d) *J. Immunol.* 161:4493–4497; Krieg (1998) *Applied Antisense Oligonucleotide Technology* Ch. 24, pp. 431–448, C. A. Stein and A. M. Krieg, Eds., Wiley-Liss, Inc.; Krieg et al. (1998a) *Trends Microbiol.* 6:23–27; Krieg et al. (1998b) *J. Immunol.* 161:2428–2434; Krieg et al. (1998c) *Proc. Natl. Acad. Sci. USA* 95:12631–12636; Spiegelberg et al. (1998) *Allergy* 53(45S):93–97; Horner et al. (1998) *Cell Immunol.* 190: 77–82; Jakob et al. (1998) *J. Immunol.* 161:3042–3049; Redford et al. (1998) *J. Immunol.* 161:3930–3935; Weeratna et al. (1998) *Antisense & Nucleic Acid Drug Development* 8:351–356; McCluskie et al. (1998) *J. Immunol.* 161(9): 4463–4466; Gramzinski et al. (1998) *Mol. Med.* 4:109–118; Liu et al. (1998) *Blood* 92:3730–3736; Moldoveanu et al. (1998) *Vaccine* 16: 1216–1224; Brazolot Milan et al. (1998) *Proc. Natl. Acad. Sci. USA* 95:15553–15558; Briode et al. (1998) *J. Immunol.* 161:7054–7062; Briode et al. (1999) *Int. Arch. Allergy Immunol.* 118:453–456; Kovarik et al. (1999) *J. Immunol.* 162:1611–1617; Spiegelberg et al. (1999) *Pediatr. Pulmonol. Suppl.* 18:118–121; Martin-Orozco et al. (1999) *Int. Immunol.* 11:1111–1118; EP 468,520; WO 96/02555; WO 97/28259; WO 98/16247; WO 98/18810; WO 98/37919; WO 98/40100; WO 98/52581; WO 98/52962; WO 98/55495; WO 98/55609; WO 99/11275; Elkins et al. (1999) *J. Immunol.* 162:2291–2298; WO 98/52962; WO 99/51259 and Van Uden et al. (1999) *J. Allergy Clin. Immunol.* 104:902–910. See also Zimmermann et al. (1998) *J. Immunol.* 160:3627–3630; Krieg (1999) *Trends Microbiol.* 7:64–65; WO 99/33488; WO 99/33868; WO 99/62923 and U.S. Pat. Nos. 5,663,153, 5,723,335 and 5,849,719. See also Liang et al. (1996) *J. Clin. Invest.* 98:1119–1129; Bohle et al. (1999) *Eur. J. Immunol.* 29:2344–2353 and WO 99/56755.

The ability to modulate the Th1-type immune response would be desirable in situations where levels of antibody production or cytokine production may be important, for example in viral infections or allergic conditions. The present invention provides compositions and methods of differential modulation of Th2-type responses to Th1-type responses.

All publications cited herein are hereby incorporated by reference in their entirety.

DISCLOSURE OF THE INVENTION

The invention provides compositions of classes (i.e., populations) of ISS-antigen conjugates with differing and distinct biological properties. The varying structural and functional characteristics are described herein and in general encompass varying average extent of conjugation and varying function, such as average modulation of immune response (particularly in terms of Th1 response), average ability to compete with antigen-specific antibody for binding to antigen, and ability to suppress histamine release (in instances in which antigen is an allergen). The various embodiments are described herein. The ISS may be any immunostimulatory sequence as described herein. The antigen may be any antigen, including allergens and antigens associated with infectious agents, such as hepatitis B virus, HIV, papillomavirus, respiratory viruses (such as influenza virus), mycobacteria, pertussis, and *Salmonella*. The antigen may also be any antigen associated with cancer, for example, a tumor antigen.

The invention also provides methods using these compositions, such as methods of modulating an immune response and methods of treating an allergic condition.

Accordingly, in one aspect, the invention provides a population of conjugate molecules, said conjugate molecules comprising an antigen and a polynucleotide comprising an immunostimulatory sequence (ISS), wherein the extent of conjugation in the population is such that the ratio of (i) concentration of ISS-antigen conjugate required for 50% inhibition of binding of antigen-specific antibody to antigen to (ii) concentration of antigen required for 50% inhibition of antigen-specific antibody to antigen is about 3.5 to about 6.0. In some embodiments, the antigen of the population is an allergen, and the extent of conjugation in the population is such that the ratio of (i) concentration of ISS-antigen conjugate required for about 40% histamine release from basophils from an antigen-sensitized individual to (ii) concentration of antigen required for about 40% histamine release from basophils from an antigen-sensitized individual is greater than about 1000.

In another aspect, the invention provides a population of conjugate molecules, said conjugate molecules comprising an antigen and a polynucleotides comprising an immunostimulatory sequence (ISS), wherein the extent of conjugation in the population is such that the ratio of (i) concentration of ISS-antigen conjugate required for 50% inhibition of binding of antigen-specific antibody to antigen to (ii) concentration of antigen required for 50% inhibition of antigen-specific antibody to antigen is about 2.5 to about 3.0. In some embodiments, the antigen of the population is an allergen, and the extent of conjugation in the population is such that the ratio of (i) concentration of ISS-antigen conjugate required for about 40% histamine release from basophils from an antigen-sensitized individual to (ii) concentration of antigen required for about 40% histamine release from basophils from an antigen-sensitized individual is about 100 to about 200.

In some aspects, the invention provides a population of conjugate molecules, said conjugate molecules comprising an antigen and a polynucleotide comprising an immunostimulatory sequence (ISS), wherein the extent of conjugation of the antigen and the polynucleotide is such that the antigen-specific antibody production in an individual receiving the conjugate population is suppressed as compared to receiving the same amount unlinked polynucleotide and antigen or the same amount of antigen alone. In some aspects, the extent of antigen-specific antibody production can be reduced or, in some aspects, eliminated.

In another aspect, the invention provides compositions comprising a population of conjugate molecules of the invention and a pharmaceutically acceptable excipient.

In another aspect, the invention provides methods for modulating an immune response in an individual comprising administering to the individual a composition comprising a population of conjugate molecules of the invention in an amount sufficient to modulate the immune response in the individual. In some aspects, modulating an immune response comprises stimulating production of a Th-1 associated cytokine. In some aspects, modulating an immune response comprises reducing production of a Th-2 associated cytokine. In some aspects, modulating an immune response comprises reducing production of antigen-specific antibodies.

In another aspect, the invention provides methods for treating an allergic condition in an individual comprising administering to the individual a composition comprising a population of conjugate molecules of the invention in an amount sufficient to palliate the allergic condition.

In another aspect, the invention provides methods for reducing antigen-stimulated IgE production in an individual comprising administering to the individual a composition comprising a population of conjugate molecules of the invention in an amount sufficient to reduce IgE production stimulated by the antigen.

In another aspect, the invention provides methods for treating an IgE-related disorder in an individual comprising administering to the individual a composition comprising a population of conjugate molecules of the invention in an amount sufficient to reduce IgE production and treat the disorder in the individual.

In another aspect, the invention provides methods for stimulating Th1 lymphocytes in an individual comprising administering to the individual a composition comprising a population of conjugate molecules of the invention in an amount sufficient to stimulate Th1 lymphocytes in the individual. In some aspects, in these individuals, production of a Th1-associated cytokine is stimulated.

In another aspect, the invention provides methods for suppressing Th2 lymphocytes in an individual comprising administering to the individual a composition comprising a population of conjugate molecules of the invention in an amount sufficient to suppress Th2 lymphocytes in the individual. In some aspects, in these individuals, production of a Th2-associated cytokine is suppressed.

BRIEF DESCRIPTION OF THE DRAWINGS

FIG. 1 is a graph depicting anti-Amb a 1 IgG1 production in mice receiving an AIC-H (i.e., a high extent of conjugation, Amb a 1 and ISS) conjugate population. Solid triangles, AIC-H; solid squares, Amb a 1. Briefly, mice were primed at week 0 with Amb a 1 in alum which generated a Th2 response. Beginning fifteen weeks later, mice were treated with Amb a 1 or AIC-H (lot 5), with 3 injections 2 weeks apart (10 μg each; indicated by arrows). IgG1 was measured using ELISA, as described in the Examples section.

FIG. 2 is a graph depicting anti-Amb a 1 IgE production in mice receiving an AIC-H conjugate population. Solid triangles, AIC-H; solid squares, Amb a 1. The experiment was conducted as described in the legend for FIG. 1. IgE was measured using ELISA.

FIG. 3 is a graph depicting anti-Amb a 1 IgG2a production in mice receiving an AIC-H conjugate population. Solid triangles, AIC-H; solid squares, Amb a 1. The experiment was conducted as described in the legend for FIG. 1. IgG2a was measured using ELISA, as described in the Examples section.

FIG. 4 is a bar graph depicting anti-Amb a 1 IgG1 (left bar) and IgG2a (right bar) production two weeks post first immunization in mice receiving AIC-H (lots BK5 and BK9), AIC-M (lots BK10 and BK12), and AIC-L (lot BK11), versus Amb a 1.

FIG. 5 is a bar graph depicting IL-5 production four weeks post second immunization in mice after receiving AIC-H (lots BK5 and BK9) compared to receiving Amb a 1.

FIG. 6 is a bar graph depicting interferon γ production four weeks post second immunization in mice receiving AIC-H (lots BK5 and BK9) compared to receiving Amb a 1.

FIG. 7 is a bar graph depicting Amb a 1-specific IgG1 (left bar) and Amb a 1-specific IgG2a (right bar) production two weeks post Amb a 1 challenge in mice having received two rounds of immunization with AIC-H (lots BK5 and BK9) prior to challenge compared to mice having received two rounds of immunization with Amb a 1 prior to challenge.

FIG. 8 is a bar graph depicting IL-5 production four weeks post Amb a 1 challenge in mice having received two rounds of immunization with AIC-H (lot BK9) prior to challenge compared to mice having received two rounds of immunization with Amb a 1 prior to challenge.

FIG. 9 is a bar graph depicting interferon γ production four weeks post Amb a 1 challenge in mice having received two rounds of immunization with AIC-H (lot BK9) prior to challenge compared to mice having received two rounds of immunization with Amb a 1 prior to challenge.

FIG. 10 is a graph comparing levels of histamine release of basophils isolated from an allergic patient ("JMW") from stimulation by Amb a 1 (solid diamond), AIC-L (solid square), AIC-M (solid triangle) or AIC-H (solid circle).

FIG. 11 is a graph comparing levels of histamine release of basophils isolated from an allergic patient ("JF") from stimulation by Amb a 1 (solid diamond), AIC-L (solid square), AIC-M (solid triangle) or AIC-H (solid circle).

FIGS. 12 (A) and (B) are half-tone reproductions of SDS-polyacrylamide electrophoresis experiments (PAGE) in which the gels were stained with Coomassie Blue (A) or silver (B). AIC-L, AIC-M, and AIC-H are labeled L, M, and H, respectively.

FIG. 13 is a graph of size-exclusion chromatographic separation of AIC-H, AIC-M and AIC-L.

MODES OF PRACTICING THE INVENTION

Figure 1:
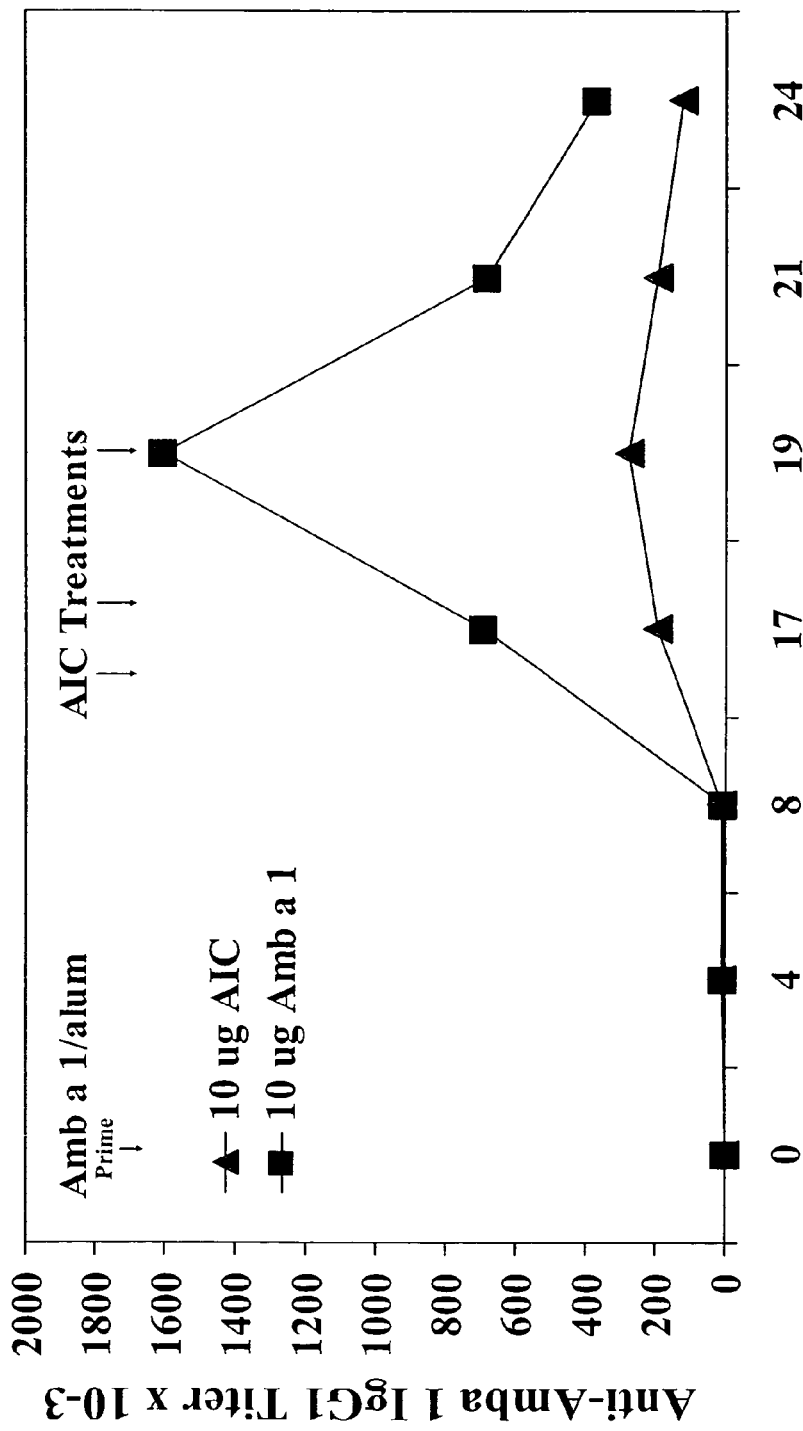
Figure 2:
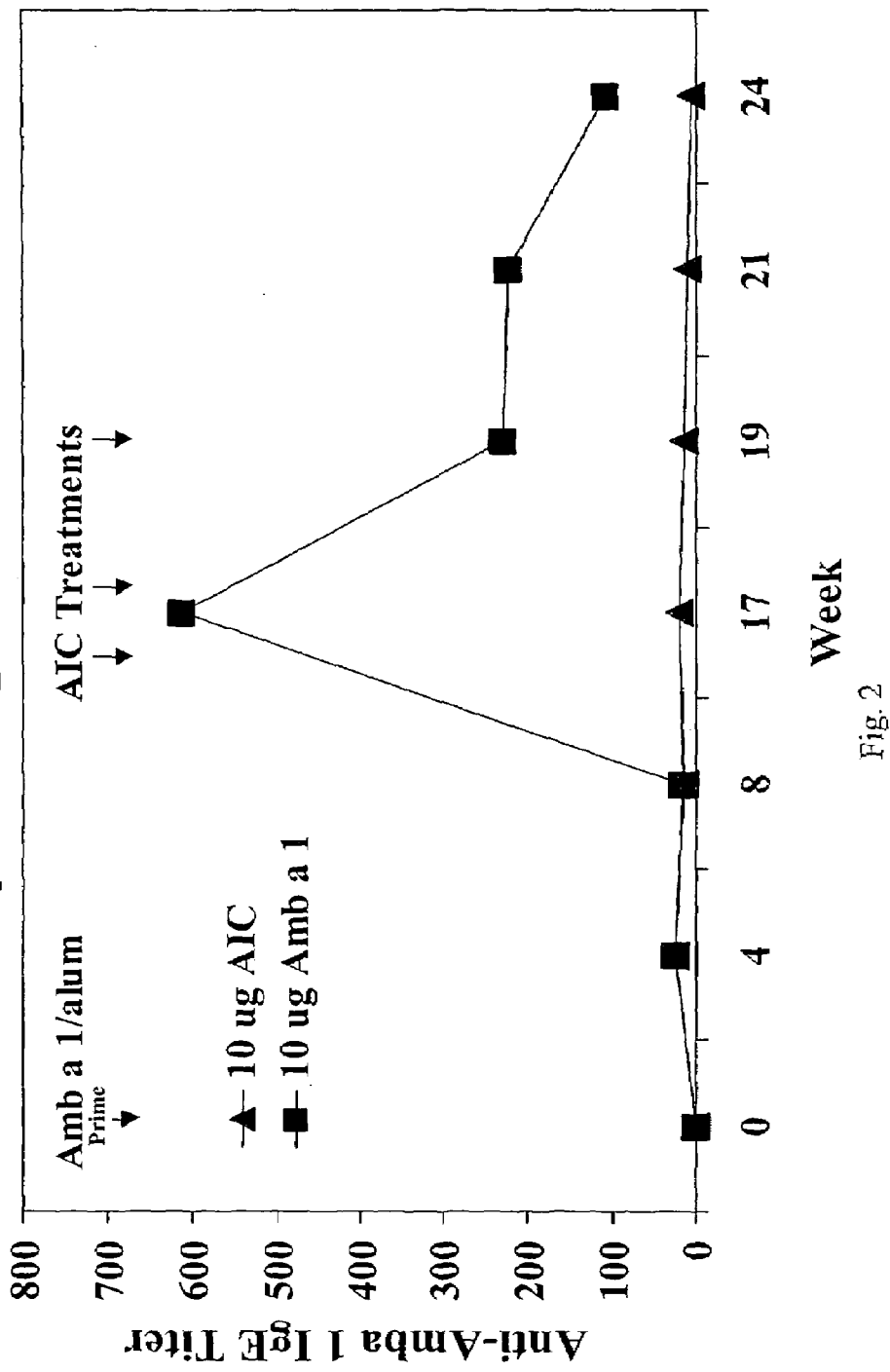
Figure 3:
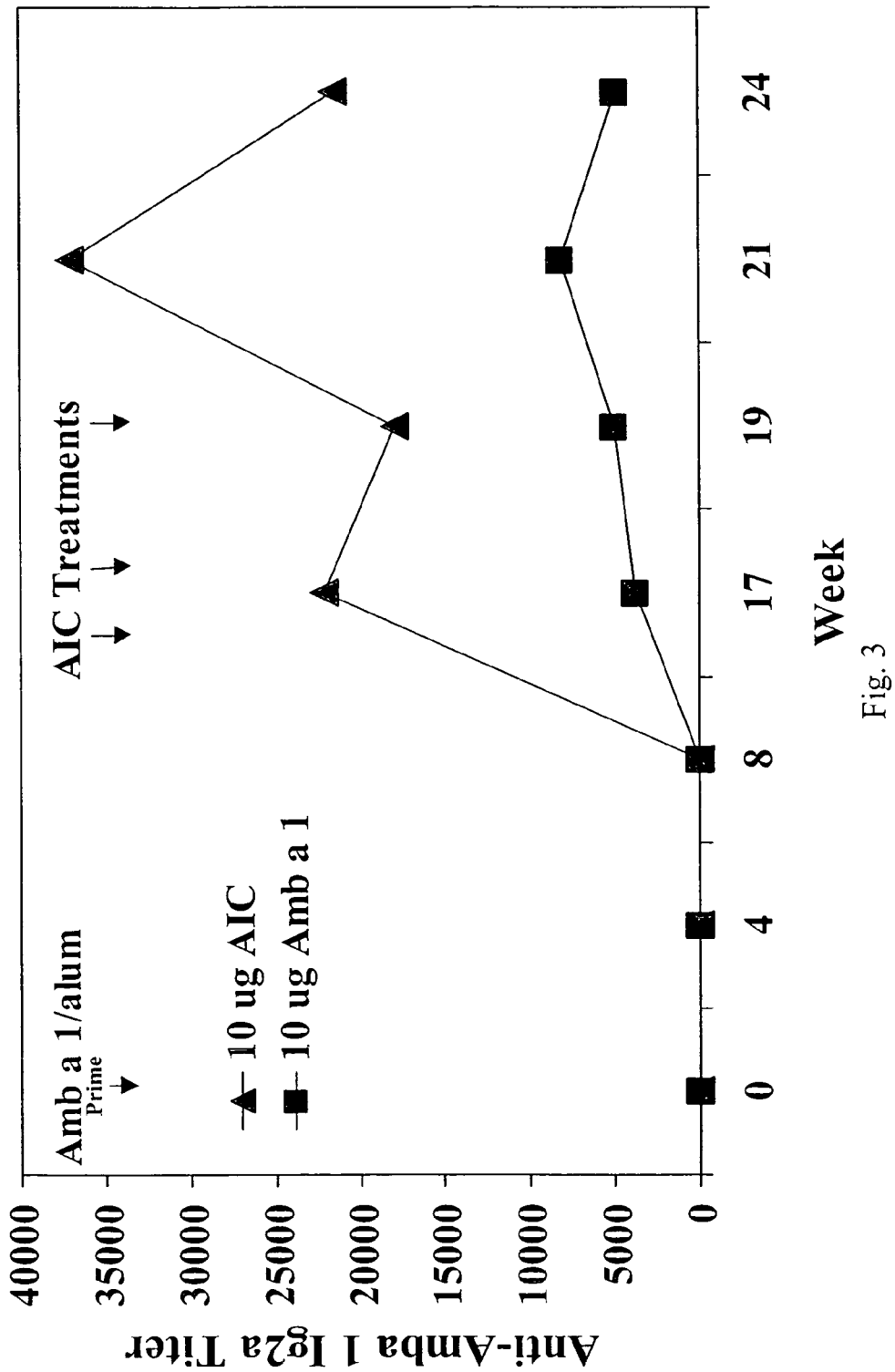
Figure 4:
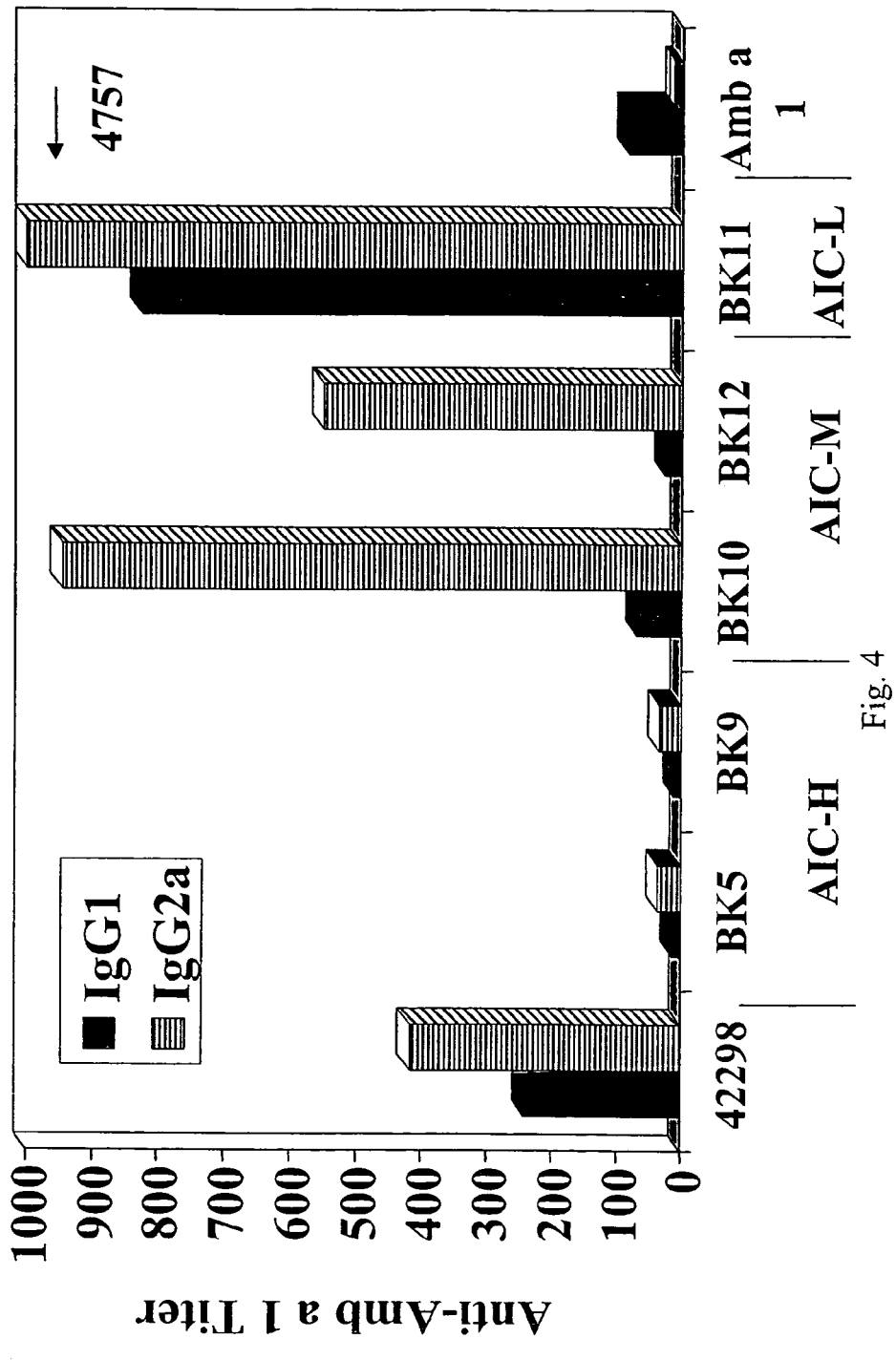
Figure 5:
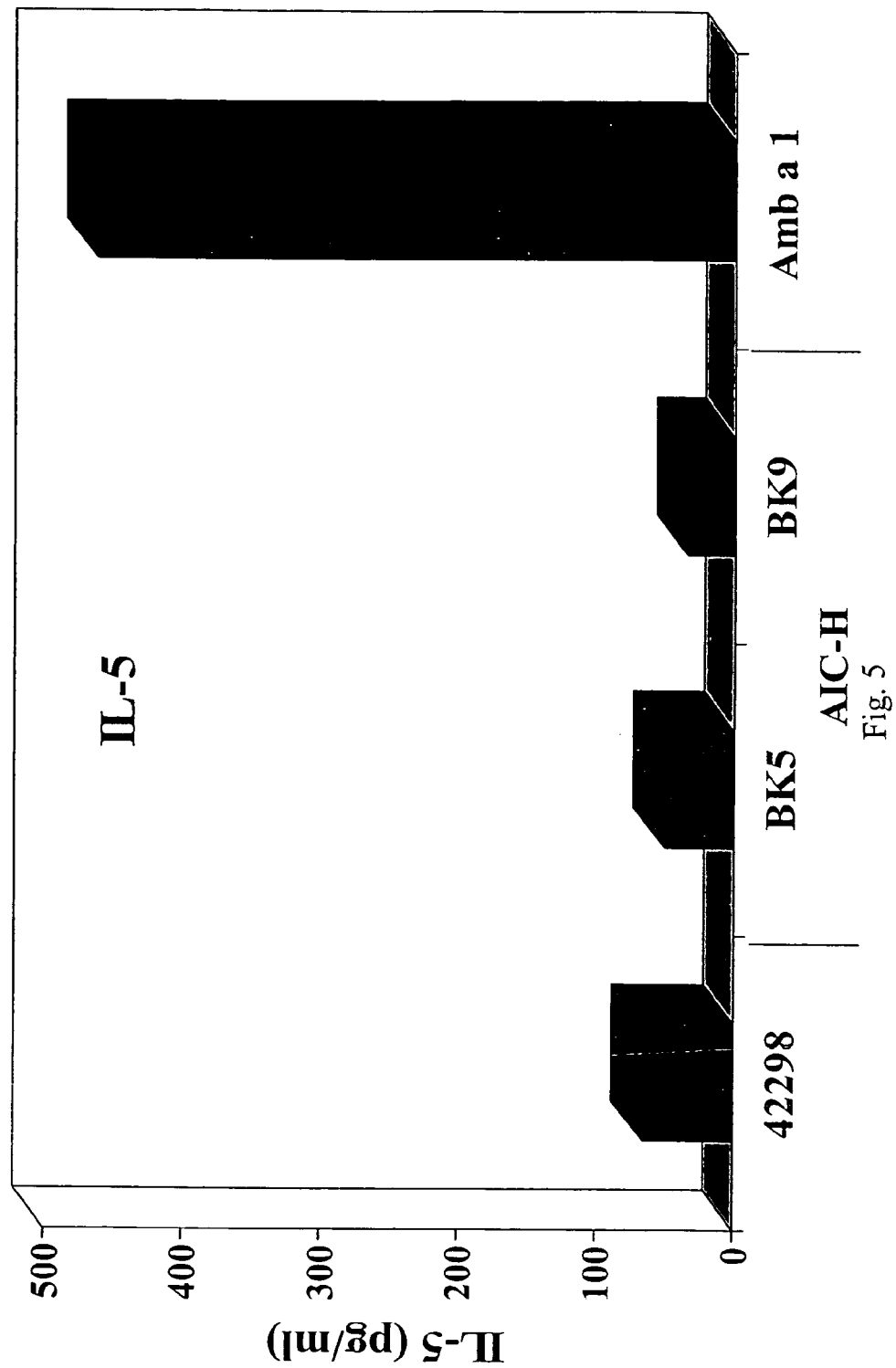
Figure 6:
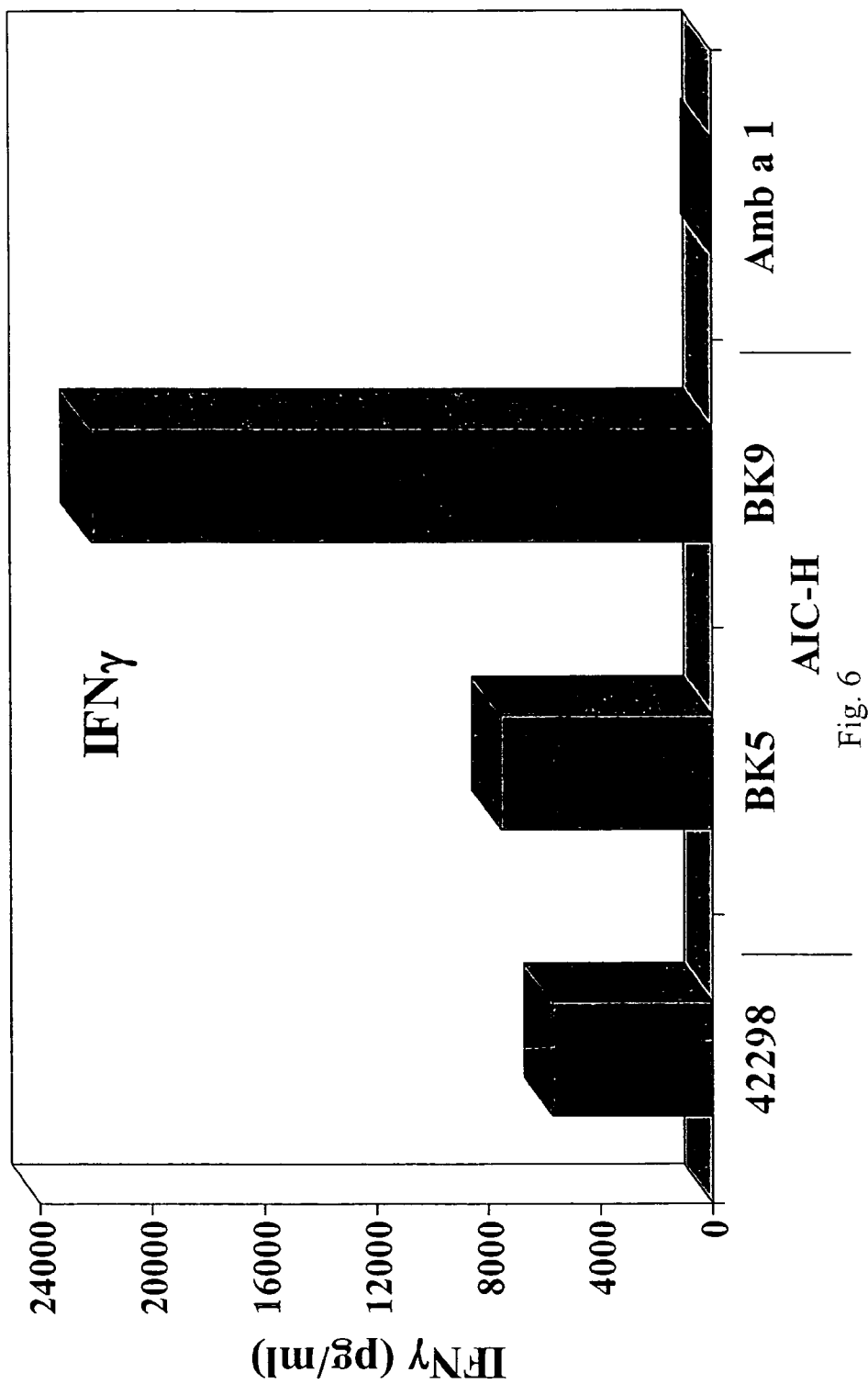
Figure 7:
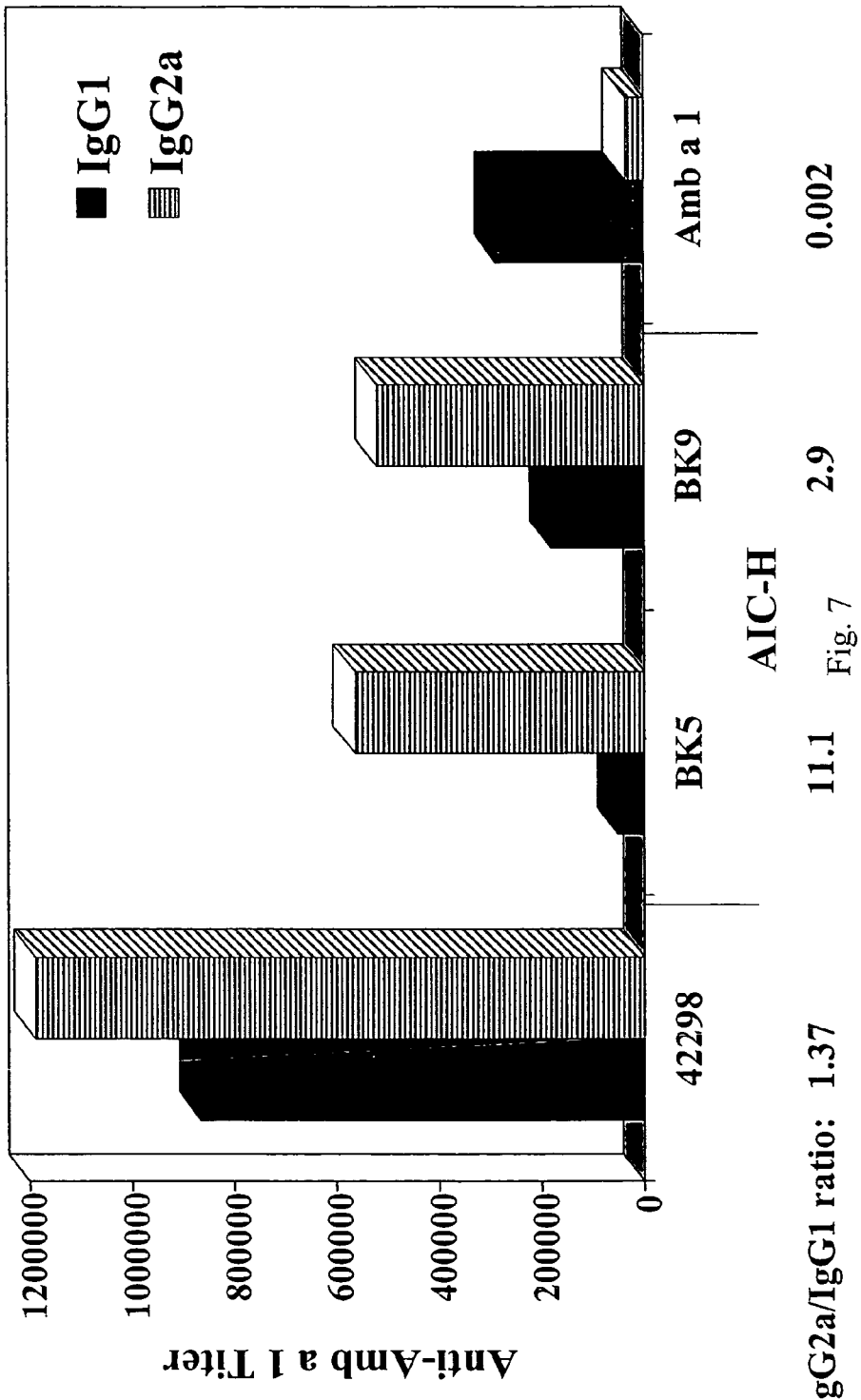
Figure 8:
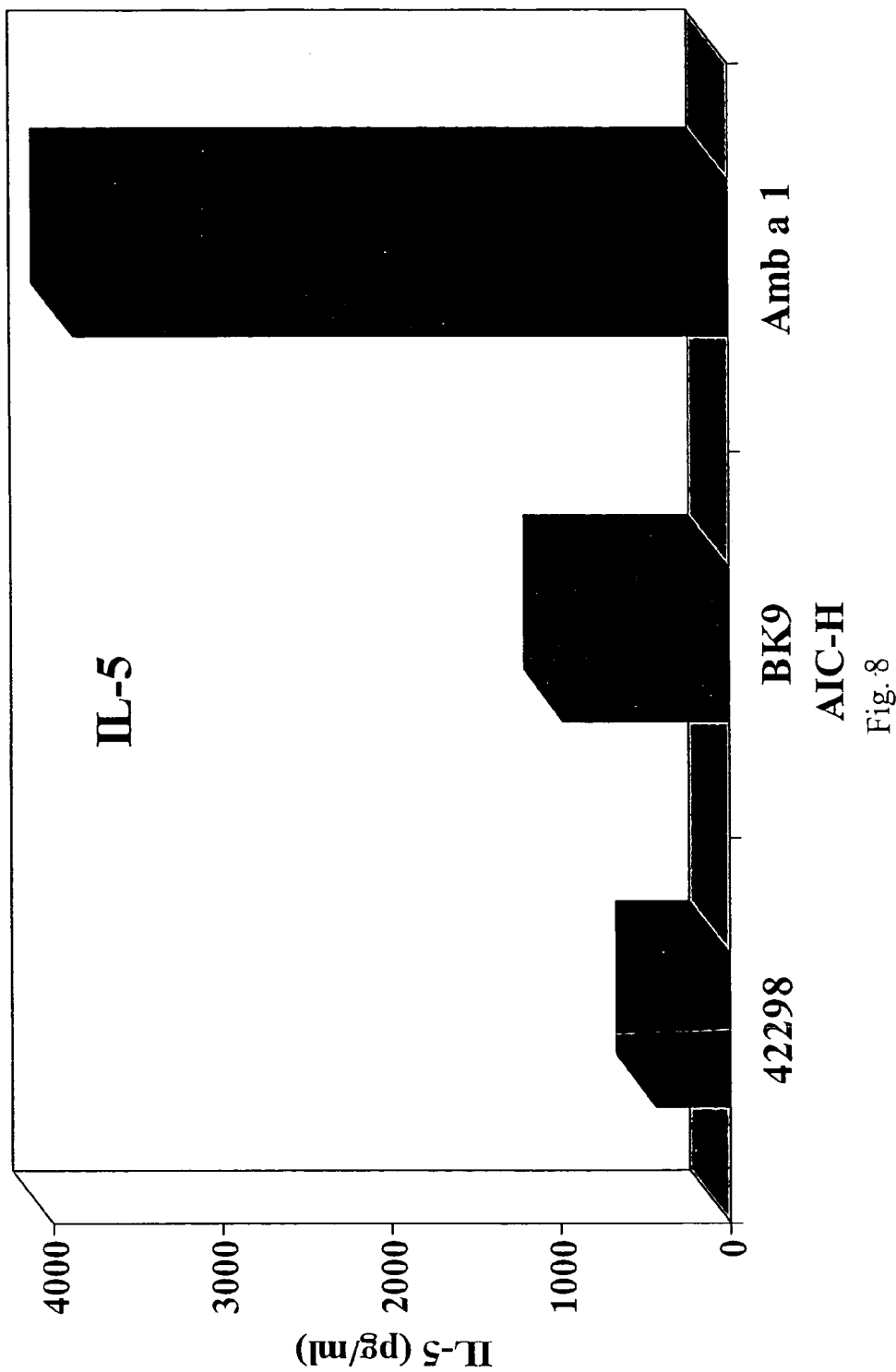
Figure 9:
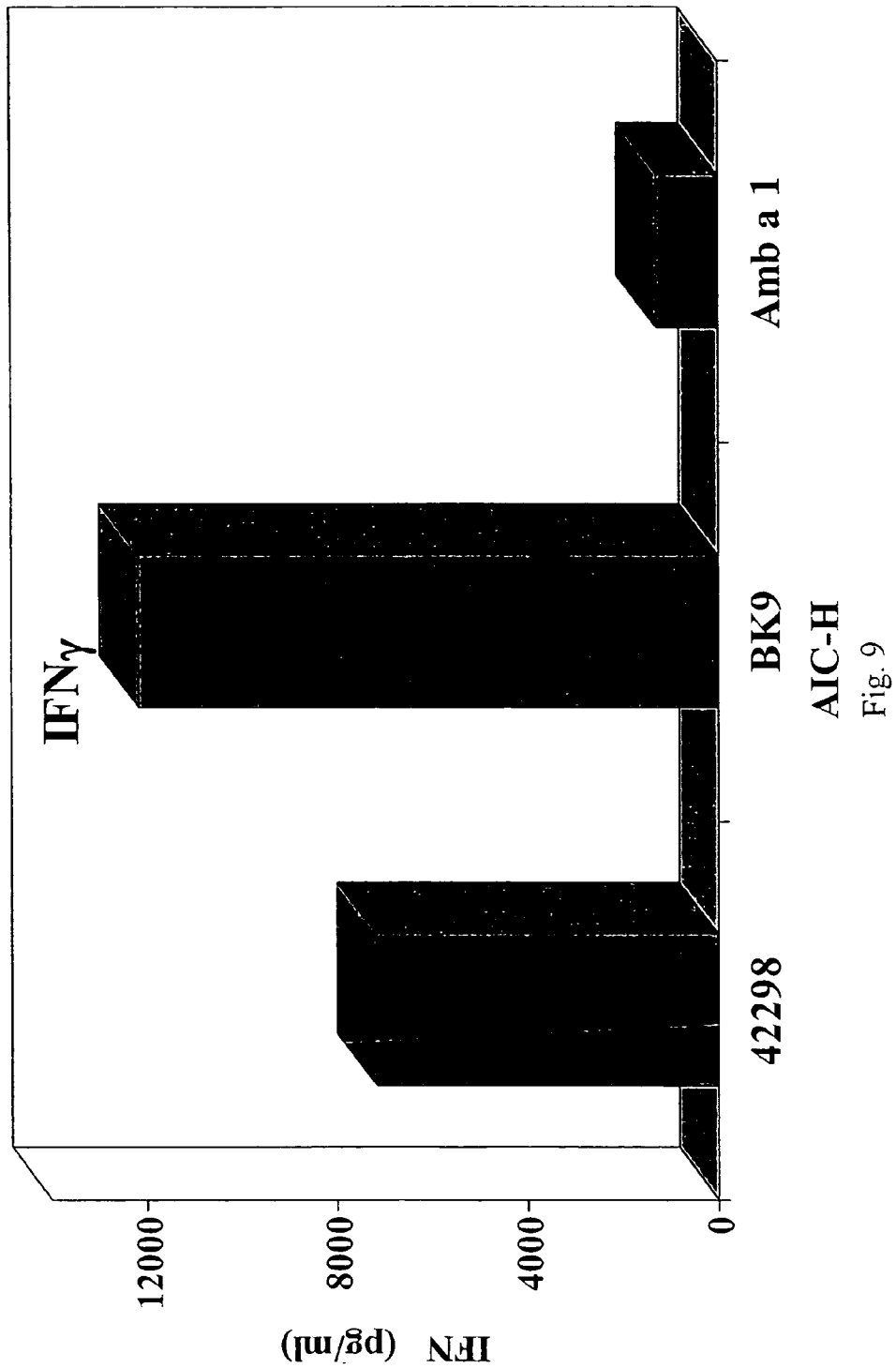
Figure 10:
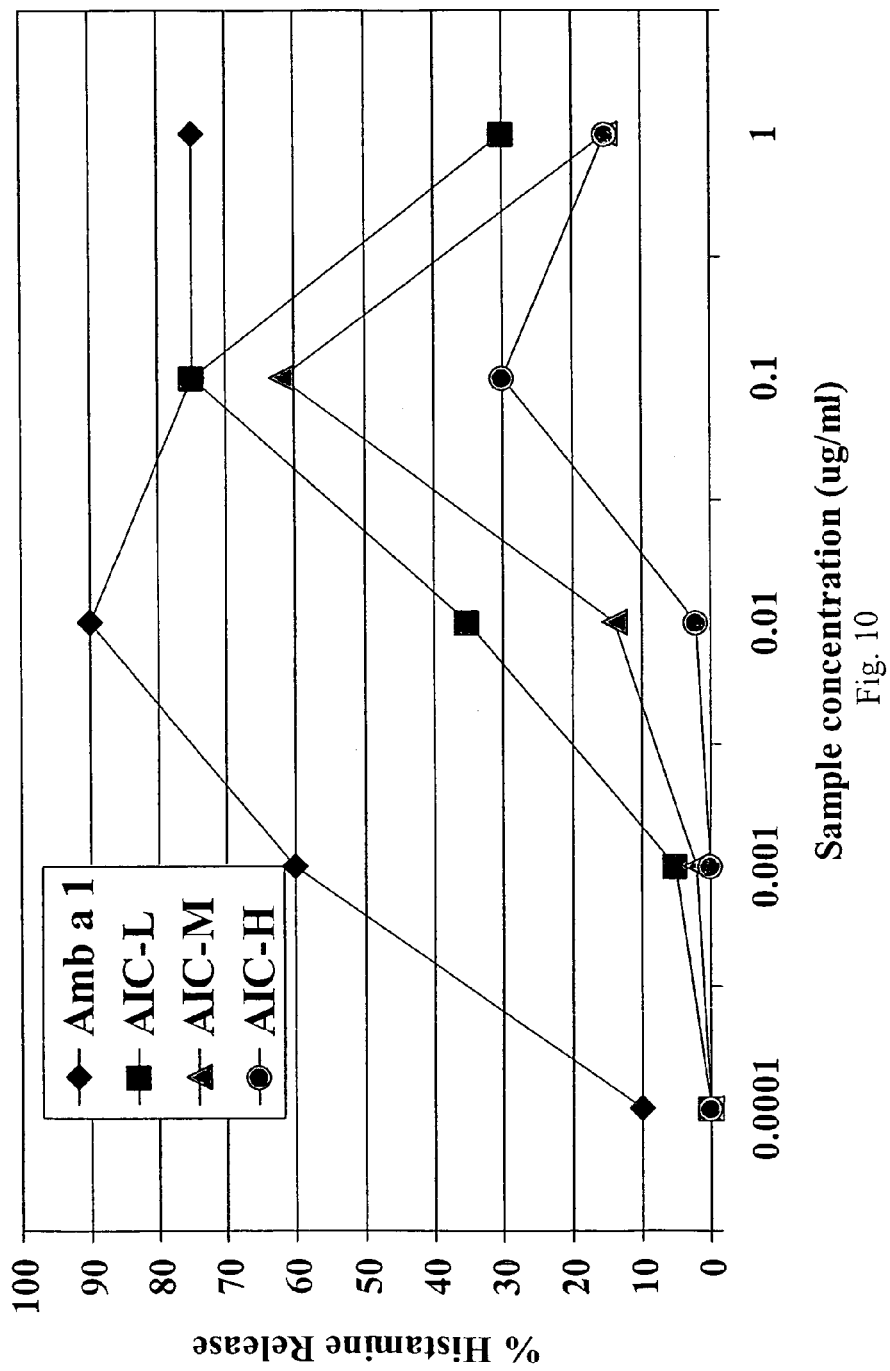
Figure 11:
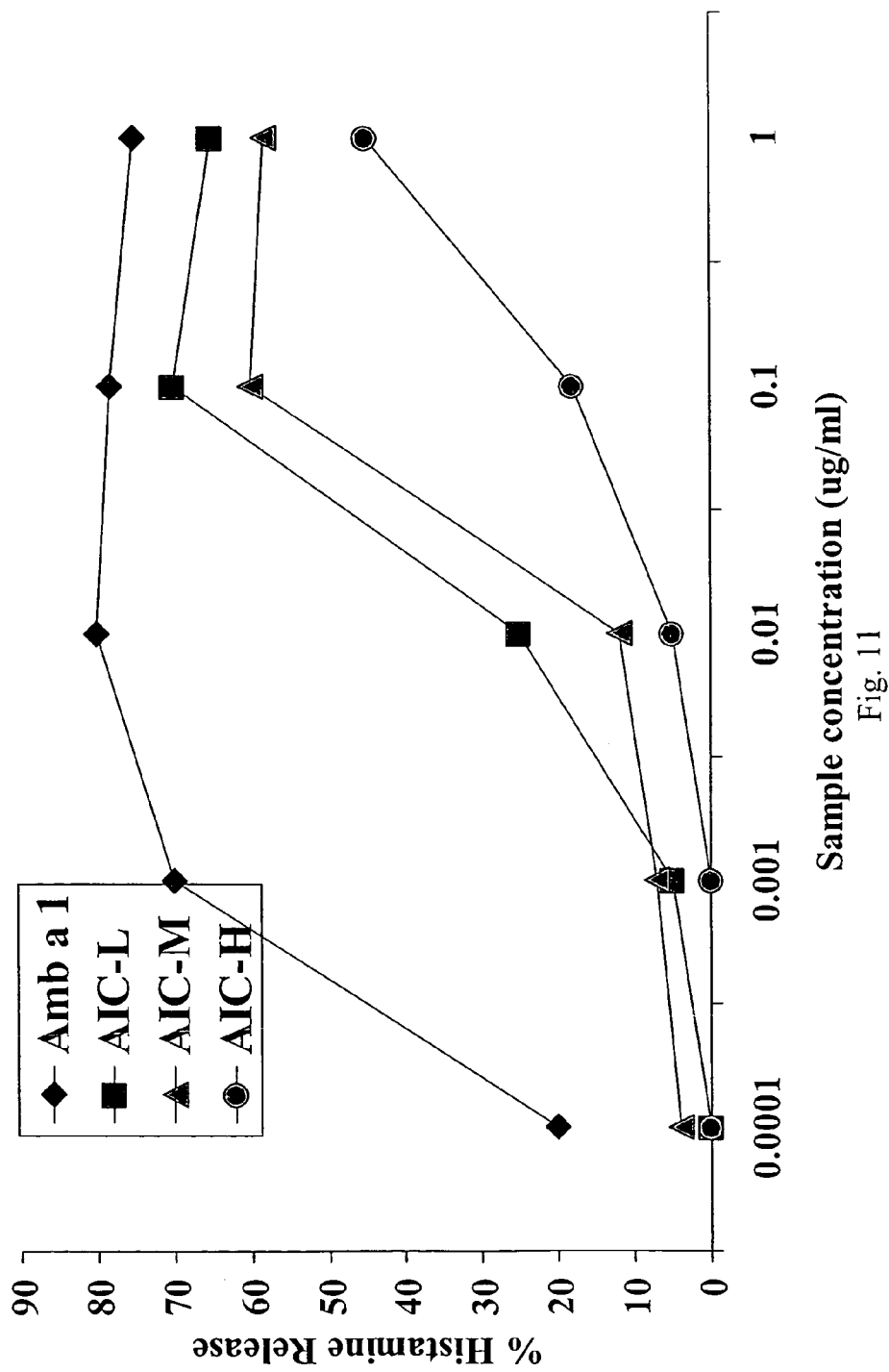

We have discovered that the extent of conjugation of polynucleotide immunostimulatory sequences (ISS) with antigen differentially modulates the immune response. For example, in particular, we have discovered that greater extent of conjugation in turn leads to suppression of overall antigen-specific antibody production while preserving a Th1 shift (i.e., Th1-associated cytokines are released). We have further discovered that more extensive conjugation is significantly effective at suppressing histamine release when an allergenic antigen is used.

As described in the Examples, different extents of conjugation of an ISS oligonucleotide to the ragweed allergen Amb a 1 creates new classes of molecules with interesting and surprising biological properties. All of these classes induce Th1 rather than Th2 responses as measured by IgG2a antibody and IFN-γ cytokine responses in mice. When compared to Amb a 1, these molecules have reduced allergenicity as measured by in vitro histamine release assays using basophils from ragweed allergic human subjects.

For ease of description and understanding, populations of ISS-antigen conjugates which differ, inter alia, in the extent of conjugation (and thus differ in one or more immunomodulatory properties), can be divided into three general classes, denoted herein as "L" (low extent of conjugation), "M" (medium extent of conjugation), and "H" (high extent of conjugation). The number of ISS molecules conjugated to the antigen affects the biological properties of the conjugate. Conjugates containing low ratios of ISS:protein ("L") induce strong Th1 responses, induce the highest antibody responses (as measured by combined measurement of Th1- and Th2-associated antibodies) and provide the least reduction in allergenicity (as measured to extent of histamine response in antigen-sensitized cells). Conjugates containing moderate ISS:antigen ratios ("M") induce strong Th1 responses, induce moderate antibody responses, and provide moderate reduction in allergenicity. Conjugates containing high ISS:antigen ratios ("H") induce strong Th1 responses, induce very low antibody responses, and provide the highest reduction in allergenicity. All three forms of the conjugates induce cytotoxic T cell activity. All three forms of the conjugates could be useful in different applications. L-form conjugates could be anticipated to be most useful in applications where a Th1 response is desired along with high antibody responses, such as in infectious disease vaccines. H-form conjugates could be anticipated to be most useful where strong Th1 responses are desired without high antibody titers, such as in allergy immunotherapy or treatment of certain cancers. M-form conjugates could be anticipated to be most useful in applications where a balance between Th1 cellular immune responses and antibody responses are desired.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993).

Definitions

As used herein, the singular form "a", "an", and "the" includes plural references unless indicated otherwise. For example, "an" ISS includes one or more The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

A "population of conjugate molecules" is a group of ISS-antigen conjugates (i.e., ISS linked, or attached, to antigen). For purposes of this invention, it is understood that such populations do not necessarily have, and may or may not have, a constant number of ISS attached to each antigen molecule. Typically, a given population will have a distribution of molecular weights (based on varying extent of conjugation within a given population) and thus an average number of ISS conjugated to antigen. It is understood that any of the populations described herein may contain molecules of free antigen (i.e., antigen not linked to ISS) and/or free ISS (i.e., ISS not linked to antigen), due to, for example, incomplete conjugation and/or purification. For purposes of this invention, the populations described herein contain conjugate molecules, but need not exclusively contain conjugate molecules.

An "average" of a given parameter (such as number of ISS-containing polynucleotides or mass) in a given population means the total of that parameter for the entire population divided by the number of members of the population. For example, the average number of ISS-containing polynucleotides attached to antigen refers to the average number of ISS-containing polynucleotides per antigen molecule in a population of conjugate molecules (i.e., total number of ISS-containing polynucleotides divided by total number of antigen molecules). As described below, this number is usually derived from weight determinations of polynucleotide to antigen, as measured, for example, by spectroscopy.

A "median" number or weight for a given population refers to a number or weight at which half the population is above, and half the population is below. For example, a median number of ISS-containing polynucleotides per antigen molecule means that half the conjugate molecules in the population have a lower number of ISS-containing polynucleotides per antigen molecule, and half have a higher number.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphoester linkages. A nucleoside consists of a purine (adenine or guanine or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "immunomodulatory" or "modulating an immune response" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, CD4$^+$ T lymphocytes, CD8$^+$ T lymphocytes, macrophages and the like; increased synthesis of immunostimulatory cytokines including, but not limited to, IL-1, IL-2, IL-4, IL-5, IL-6, IL-10, IL-12, IFN-$\alpha$, IFN-$\beta$, IFN-$\gamma$, TNF-$\alpha$ and the like. Immunosuppressive effects include those that directly or indirectly decrease cellular or humoral immune responses. Examples of immunosuppressive effects include, but are riot limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-$\gamma$, which appears to block IL-4 induced class switch to IgE and IgG1, thereby reducing the levels of these antibody subclasses.

The term "conjugate" refers to a complex in which an ISS-containing polynucleotide and an antigen are linked. Such conjugate linkages include covalent and/or non-covalent linkages.

"Extent of conjugation" means the average degree conjugation in a given population. As described herein, extent of conjugation may be characterized by any of a number structural and/or functional parameters, either alone or in any combination.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with ISS include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in Hemophilus influenza vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are of at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant proteins, crude protein extracts, attenuated or inactivated viruses, cells, microorganisms, or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an ISS and/or antigen to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111–127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of a composition comprising an ISS-antigen conjugate is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *hymenoptera*sting allergies, and drug allergies, and parasite infections. The term also includes related manifestations of these disorders. Generally, IgE in such disorders is antigen-specific.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an ISS-antigen conjugate or antigen refers to the amount of a given antibody measured at a time point after administration of conjugate or antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a conjugate population which suppresses histamine release reduces histamine release as compared to, for example, histamine release induced by antigen alone. As another example, a conjugate population which suppresses antibody production reduces extent and/or levels of antibody as compared to, for example, extent and/or levels of antibody produced by antigen alone.

COMPOSITIONS OF THE INVENTION

Conjugate Populations with Varying Structural and Immunomodulatory Properties

Generally, the classes, or populations, of conjugate molecules of the invention and described herein may be distinguished and/or defined by any of a number of structural and/or functional properties, including:

(a) average number of ISS-containing polynucleotides attached or linked to antigen;

(b) median number of ISS-containing polynucleotides attached or linked to antigen;

(c) ratio of average mass of ISS-containing polynucleotide to average mass of antigen;

(d) ratio of median mass of ISS-containing polynucleotide to median mass of antigen;

(e) ratio of (i) concentration of ISS-antigen conjugate required for inhibition of binding of antigen-specific antibody to antigen to (ii) concentration of antigen required for the same extent of inhibition of antigen-specific antibody to antigen (as discussed below, these ratios are usually, but need not be, calculated at 50% inhibition);

(f) for antigens which are allergens, the ratio of (i) concentration of ISS-antigen conjugate required for histamine release from basophils from an antigen-sensitized individual to (ii) concentration of antigen required for the same extent of histamine release from basophils from an antigen-sensitized individual (as discussed below, these ratios may be, but need not be, calculated at about 40% histamine release);

(g) ratio of (i) the sum of Th1-associated antibodies and Th2-associated antibodies elicited by ISS-antigen conjugate to (ii) the sum of Th1-associated antibodies and Th2-associated antibodies elicited by antigen;

(h) ratio of (i) Th1-associated antibodies elicited by ISS-antigen conjugate to (ii) ratio of Th2-associated antibodies elicited by ISS-antigen conjugate;

(i) different cytokine production profiles when compared to antigen alone;

(j) extent of suppression of antigen-specific antibody production, as described above in "Modes of Practicing the Invention".

All of these classes and embodiments described herein may be described and/or defined by one, more than one, and/or any combination of the properties listed above. Accordingly, the invention provides populations of conjugate molecules, said conjugate molecules comprising an antigen and one or more polynucleotides comprising an immunostimulatory sequence (ISS), wherein said populations comprises any one or more of the properties described herein, either alone or in any combination. The properties (including ratios) may be measured using standard techniques in the art and described herein, and it is understood that any of these properties may be measured in a variety of systems, including in vivo systems such as vertebrates and mammals, including, for example, mouse and/or human.

In accordance with the above, for example, and based on observations pertaining to a conjugate of Amb a 1 and an ISS-containing 22-mer polynucleotide (5'-TGACTGT-GAACGTTCGAGATGA-3', SEQ ID NO:1), the "H" class is defined by any of the following properties, either alone or in any combination:

(a) an average of at least about 5.5, more preferably 6, ISS-containing polynucleotides per antigen molecule;

(b) ratio of (i) average mass of ISS-containing polynucleotide to (ii) average mass of antigen is (i) about or alternatively at least about 35, 40 or 45 to (ii) about 40;

(c) ratio of (i) concentration of ISS-antigen conjugate required for 50% inhibition of binding of antigen-specific antibody to antigen to (ii) concentration of antigen required for 50% inhibition of binding of antigen-specific antibody to antigen is about 3.5 to about 6.0 or more (including, but not limited to, 7.0, 8.0, 9.0, 10.0, 15, 20, 25, 30, 35, 40, 45, 50 or more) or alternatively is at least about any of the following: 3.5, 4.0, 4.5, 5.0, 5.5, 6.0, 6.5, 7.0, 8.0, 9.0, 10, 15, 20, 25 (if expressed as a range, the upper limit may be any number, including those listed);

(d) for embodiments in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is greater than about 300, preferably greater than about 500, preferably greater than about 750, more preferably greater than about 1000, more preferably greater than about 1250, more preferably greater than about 1400, more preferably greater than about 1500 (with an upper limit being any number, including, but not limited to, 750, 1000, 1250, 1500, 1750, 2000, 2250, 2500, 2750, 3000, 3500, 4000, 4500, 5000, 5500, 6000);

(e) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of unit mass of antigen administered) is about or alternatively is less than about any of the following: 10, 7, 5, 4, 3.5, 3.0; 2.5, 2.0, 1.5, 1.0, 0.75, 0.5, 0.4, 0.3, 0.2, 0.1.

(f) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of 10 times the unit mass of antigen administered compared to amount conjugate administered) is about or alternatively is less than about any of the following: 1.0, 0.7, 0.6, 0.5, 0.4, 0.35; 0.3; 0.25, 0.2, 0.15, 0.11, 0.075, 0.05, 0.04, 0.03, 0.02, 0.01.

(g) ratio of (i) titer of Th1-associated antibodies elicited by ISS-antigen conjugate (in terms of antibodies elicited per unit mass of conjugate administered) to (ii) titer of Th1-associated antibodies elicited by antigen (in terms of unit mass of antigen administered compared to amount conjugate administered) is about or alternatively is less than about any of the following: 60, 55, 50, 45, 40, 35, 30, 25, 20, 15, 10, 5;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate about or alternatively is greater than about any of the following: 4.0, 4.5, 5.0, 5.5, 6.0, 6.5, 7.0, 7.5, 8.0, 8.5, 9.0, 9.5, 10. If expressed as a range, the upper limit may be any number, including those listed, as well as others, such as 15, 20, 25, 30, 40, 50, 60, 75, 80, 90, 100;

(i) suppression of antigen-specific antibody production (including production of Th1-associated and/or Th2-associated antibodies) as compared to administration of the same amount of unlinked ISS-containing polynucleotide and antigen or compared to administration of the same amount of antigen alone.

The "M" class is defined by any of the following properties, either alone or in any combination:

(a) an average of from about 3 to about 5 ISS-containing polynucleotides per antigen molecule;

(b) ratio of (i) average mass of ISS-containing polynucleotide to (ii) average mass of antigen is (i) about 20, about 25, or about 30 to (ii) about 40;

(c) ratio of (i) concentration of ISS-antigen conjugate required for 50% inhibition of binding of antigen-specific antibody to antigen to (ii) concentration of antigen required for 50% inhibition of antigen-specific antibody to antigen is about 2.5 to about 3.0 or alternatively about 3.25;

(d) for embodiments in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is about 100 to about 200, or, alternatively, about 100, or alternatively, about between about 75 to about 250.

(e) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of unit mass of conjugate administered) is about 13 or alternatively is between about 10 or about 12 to about 100 (or, in some embodiments, about 12 to about 50);

(f) ratio of titers of total Th1- and Th2-associated antibodies elicited by ISS-antigen conjugate (in terms of antibodies elicited per unit mass of conjugate administered) to total Th1- and Th2-associated antibodies elicited by antigen (in terms of 10 times the unit mass of conjugate administered compared to amount conjugate administered) is about 1.3 or alternatively is between about 1.0 or about 1.20 to about 10 (or, in some embodiments, about 1.2 to about 5.0);

(g) ratio of (i) titer of Th1-associated antibodies elicited by ISS-antigen conjugate (in terms of antibodies elicited per unit mass of conjugate administered) to (ii) titer of Th1-associated antibodies elicited by antigen (in terms of unit mass of antigen administered compared to amount conjugate administered) is between about 70 to about 500;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate is about two to about 4.

The "L" class is defined by any of the following properties, either alone or in any combination:

(a) an average of less than about 3 ISS-containing polynucleotides per antigen molecule;

(b) ratio of (i) average mass of ISS-containing polynucleotide to (ii) average mass of antigen is (i) about 15 or alternatively less than about 15 (in some embodiments, about 10 or alternatively less than about 10) to (ii) about 40;

(c) ratio of (i) concentration of ISS-antigen conjugate required for 50% inhibition of binding of antigen-specific antibody to antigen to (ii) concentration of antigen required for 50% inhibition of antigen-specific antibody to antigen is less than about 2.0, or alternatively is about 2.0;

(d) for embodiments in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is less than about 75, or, alternatively, about 75 (in other embodiments, less than about 60 or alternatively about 60) to about 200, or, alternatively, to about 100;

(e) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of unit mass of conjugate administered) is about 150, or alternatively, greater than about any of the following: 100, 150, 200, 250, 300, 350, 400, 450, 500, 550, 600, 650, 700, 750, 800. If expressed as a range, the upper limit may be any number, including the numbers listed.

(f) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of 10 times the unit mass of conjugate administered compared to amount conjugate administered) is about or alternatively is greater than about any of the following: 10, 12, 15, 20, 25, 30, 35, 40, 45, 50, 55, 60, 65, 70, 75, 80;

(g) ratio of (i) titer of Th1-associated antibodies elicited by ISS-antigen conjugate (in terms of antibodies elicited per unit mass of conjugate administered) to (ii) titer of Th1-associated antibodies elicited by antigen is about 500 or more, including, but not limited to, about 500 or more, about 600 or more, about 700 or more, about 800 or more, about 900 or more, about 1000 or more. If expressed as a range, the upper limit may be any number, including, but not limited to, 600, 700, 800, 900, 1000, 1250, 1500, 1750, 2000, 2500, 3000, 3500, 400, 4500, 5000;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate is about or alternatively is less than about any of the following: 2.0, 1.5, 1.25.

As is clear from the description herein, it is understood that any of a number of populations of conjugates could be produced, and that the classifications of "L", "M", and "H" are several examples of classes of conjugate populations. The ability to vary and control the extent of conjugation and thus control the type of modulation of the immune response extends to other populations in addition to those exemplified herein. Given the readily measurable structural and functional characteristics, it is well within the skill of the art to develop any of a number of populations. Accordingly, the invention also includes conjugate populations characterized by any of the following (either alone or in any combination):

(a) ratio of (i) concentration of ISS-antigen conjugate required for 50% inhibition of binding of antigen-specific antibody to antigen to (ii) concentration of antigen required for 50% inhibition of antigen-specific antibody to antigen is any of more than about 1.5, 2.0, 2.25, 3.0, 3.25, 3.5, 3.75, 4.0, 4.25, 4.50, 4.75, 5.0, 5.25, 5.5, 5.75, 6.0, 6.5, 7.0, 7.5, 8.0, 8.5, 9.0, 9.5, 10.0. If expressed as a range, the upper limit may be any number, including those listed (for example, the conjugate population may be more than about 2.0, more than about 2.0 and less than about 5.5, more than about 2.0 and less than about 20.0).

(b) ratio of (i) concentration of ISS-antigen conjugate required for 50% inhibition of binding of antigen-specific antibody to antigen to (ii) concentration of antigen required for 50% inhibition of antigen-specific antibody to antigen is any of less than about 1.5, 2.0, 2.25, 3.0, 3.25, 3.5, 3.75, 4.0, 4.25, 4.50, 4.75, 5.0, 5.25, 5.5, 5.75, 6.0, 6.5, 7.0, 7.5, 8.0, 8.5, 9.0, 9.5, 10.0. If expressed as a range, the lower limit may be any number listed as well as zero (for example, the conjugate population may be less than about 5.0, or alternatively less than about 5.0 and more than about 2.0).

(c) in instances where the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is at least about any of the following: 2, 5, 10, 15, 20, 25, 30, 35, 40, 45, 50, 60, 75, 80, 90, 95, 100, 120, 130, 140, 150, 175, 200, 225, 250, 275, 300, 350, 400, 450, 500, 550, 600, 650, 700, 750, 800, 850, 900, 950, 1000, 1100, 1200, 1500, 1750, 2000, 2250, 2500, 2750, 3000, 3250, 3500, 3750, 4000, 4250, 4500, 4750, 5000. If expressed as a range, the upper limit may be any number, including those listed. Alternatively, this ratio may be less than about any of the following: 2, 5, 10, 15, 20, 25, 30, 35, 40, 45, 50, 60, 75, 80, 90, 95, 100, 120, 130, 140, 150, 175, 200, 225, 250, 275, 300, 350, 400, 450, 500, 550, 600, 650, 700, 750, 800, 850, 900, 950, 1000, 1100, 1200, 1500, 1750, 2000, 2250, 2500, 2750, 3000, 3250, 3500, 3750, 4000, 4250, 4500, 4750, 5000. If expressed as a range, the lower limit may be any number listed as well as zero.

(d) ratio of antibody titer (more particularly, IgG titer, such as the sum of Th1- and Th2-associated IgG titer)

elicited per unit mass of ISS-antigen conjugate to antibody titer (more particularly, IgG titer, such as the sum of Th1- and Th2-associated IgG titer) elicited per unit mass of antigen as at least more than about any of the following: 0.1, 0.2, 0.3, 0.4, 0.5, 0.75, 1, 2, 5, 10, 15, 25, 50, 75, 100, 125, 150, 175, 200, 250, 300, 350, 400, 450, 500, 550, 600, 650, 700, 750, 800, 850, 900, 1000, 1250, 1500, 2000, 2250, 2500, 2750, 3000. If expressed as a range, the upper limit may be any number, including those listed. Alternatively, the ratio may be less than about any of the following: 0.1, 0.2, 0.3, 0.4, 0.5, 0.75, 1, 1.5, 2, 2.5, 3, 4, 5, 6, 7, 8, 9, 10, 15, 25, 50, 75, 100, 125, 150, 175, 200, 250, 300, 350, 400, 450, 500, 550, 600, 650, 700, 750, 800, 850, 900, 1000, 1250, 1500, 2000, 2250, 2500, 2750, 3000. If expressed as a range, the lower limit may be zero or any of the numbers listed.

(e) ratio of Th1-associated antibody titer elicited by conjugate to Th2-associated antibody titer elicited by conjugate (per unit mass) as less than about any of the following: 20, 15, 12, 10, 7, 5, 4.5, 4.25, 4.0, 3.75, 3.5, 3.25, 3.0, 2.5, 2.0, 1.5, 1.25, 1.0, 0.5. If expressed as a range, the lower limit may be any number listed, including zero. Alternatively, this ratio may be greater than any of the following: 0.5, 0.75, 1.0, 1.25, 1.5, 2.0, 2.5, 3.0, 3.25, 3.5, 4.0, 4.5, 5.0. If expressed as a range, the upper limit may be any number, including those listed.

(f) ratio of Th1-associated antibody titer elicited by conjugate to Th1-associated antibody titer elicited by antigen (per unit mass) is less than about any of the following: 5000, 4500, 4000, 3500, 3000, 2500, 2000, 1500, 1000, 900, 800, 700, 600, 500, 400, 300, 200, 150, 100, 50, 75, 60, 50, 40, 45, 30, 35, 25, 20, 14, 10, 5. If expressed as a range, the lower limit may be any number listed, including zero. Alternatively, this ratio may be more than about any of the following: 10, 20, 50, 60, 75, 100, 150, 200, 250, 3.00, 350, 400, 450, 500, 750, 800, 1000, 1250, 1500, 1750, 2000, 2250, 2500, 3000, 3500, 4000, 4500, 5000. If expressed as a range, the upper limit may be any number, including those listed.

The extent of conjugation can be controlled in a number of ways, all of which use chemical techniques well known in the art, which are also described herein. One way to control extent of conjugation is to vary the equivalents of ISS in relation to linkage sites on antigen. That is, a constant amount or number of linkage sites is reacted with a particular amount of ISS. For the ISS-Amb a I conjugates exemplified herein, for example, based on maleimide-activated Amb a 1, reaction with 4 molar equivalents of 5' thio ISS, 7 molar equivalents of 5' thio ISS, and 17 molar equivalents of 5' thio ISS with 1 molar equivalent of Amb a 1 gave rise to "L", "M", and "H" populations, respectively. Another way of controlling extent of conjugation is to saturate the reaction with ISS and vary the amount of available linkage sites on antigen. The linkage sites could be controlled by, for example, choosing a certain linkage moiety that gave the desired number of linkage sites (for example, choosing to link via a carbohydrate as opposed to via amino groups), or alternatively, by controlling a linkage activating reaction such that the desired average number of linkage sites are activated.

Generally, a given antigen has a maximum number of potential linkage sites, depending on the nature of the antigen-ISS linkage. The extent of conjugation can be controlled by the number of these linkage sites which are used to link an ISS. Accordingly, the invention also includes embodiments in which the average percentage of total number of linkage sites attached to an ISS-containing polynucleotide is at least about any of the following: 5%, 10%, 20%, 30%, 33%, 40%, 45%, 50%, 55%, 60%, 65%, 70%, 75%, 80%, 82%, 85%, 88%, 90%, 92%, 95%, 97%, 98%. Alternatively, the invention also includes embodiments in which the average percentage of total number of linkage sites attached to an ISS-containing polynucleotides is less than about any of the following: 10%, 20%, 30%, 33%, 40%, 45%, 50%, 55%, 60%, 65%, 70%, 75%, 80%, 82%, 85%, 88%, 90%, 92%, 95%, 97%, 98%. The total number of linkage sites is determined by the mode of attachment. For example, if an antigen is linked to ISS-containing polynucleotide via a free amino group (such as in lysine), the total number of linkage sites is the number of lysines. If antigen is linked via a sulfydryl group (such as via cysteine), then the total number of linkage sites is the total number of free sulfydryl groups. If antigen is linked via a carbohydrate moiety, then the total number of linkage sites is the total number of carbohydrate moieties. With respect to any of these embodiments, the average percentage of linkage sites attached to ISS-containing polynucleotide may be accompanied by any of the immunomodulatory characteristics listed above, alone or in combination.

Characterization of Classes of ISS-Antigen Conjugates

Conjugate populations of the invention may be identified and/or characterized by any of a number of ways, including those listed above. For example, in terms of structure, the extent of conjugation may be described by: (a) average or, alternatively median number of ISS to antigen molecules; (b) ratio of ISS to total linkage sites in antigen; (c) ratio of mass (whether average or median) of ISS to mass (whether average or median) of antigen; (d) ratio of ISS to T-cell epitopes in antigen; (e) ratio of ISS to B cell epitopes in antigen. In terms of function, which includes, but is not limited to, immune modulation, conjugate populations of the invention may be characterized in terms of (a) degree of antigen-specific antibody response, such as IgG response; (b) ratio of Th1-associated antibodies to Th2-associated antibodies; (c) degree of suppression of histamine release; (d) degree of competition with antigen-specific antibody for binding to antigen; (e) degree of suppression of Th2-associated immune response; (f) secretion of Th1-associated cytokines, such as interferon; (g) secretion of Th2-associated cytokines, such as IL-4 and/or IL-5.

Structural Characterization

The extent of ISS-antigen conjugation may be determined using any number of protein and nucleic acid measurement methods known in the art. For example, antigen and/or protein-specific detection techniques (for example, antigen-specific antibodies and/or Coomassie Blue stain) and nucleic acid-specific detection techniques (for example, hybridization with detectably-labeled DNA probes) may be used to analyze conjugation reaction products. With the use of appropriate quantitation standards, the amount of polynucleotide to antigen may be determined.

The amount of oligonucleotide bound to a polypeptide may also be determined by the measurement of size or molecular weight of the conjugate. Conjugate size may be determined using methods known in the art including, but not limited to, sodium dodecylsulfate polyacrylamide electrophoresis (SDS-PAGE) analysis and size-exclusion chromatography (SEC).

The ISS-antigen conjugates may be analyzed using a combination of size determination and/or separation techniques and nucleic acid and protein determination techniques. For example, after fractionation of conjugate reaction products using SEC, the protein and nucleic acid content of each fraction may be determined by the absorbance of the fraction at 280 nm and 260 nm, respectively. In this way, the results of both the size of the conjugate and the nucleic acid and protein detection analysis may be combined to characterize the structure of the conjugate. The ratio of the amount of polynucleotide to the amount of protein in each conjugate fraction indicates the average number of ISS molecules per antigen molecule.

Functional Characterization

Various methods known in the art may be used to determine antigen-specificity and antibody class and/or subclass of the antibodies generated in response to administration of ISS-antigen conjugates. For example, standard ELISA format assays may be used to detect and measure the amount, specificity and/or type of antibody produced in response to various ISS-antigen conjugates. In such assays, for example, antigen is attached to a substrate and incubated with serum from a ISS-antigen conjugate treated individual. The amount of antigen-specific antibody attached to the substrate-bound antigen is then determined using antibody-specific reagents, such as antibodies specific for IgG1, IgG2, IgG3, IgG4, IgE, etc.

Methods known in the art may be used to determine a concentration of ISS-antigen conjugate required for inhibition of binding of antigen-specific antibodies to antigen, such as competitive ELISA assays as described herein.

Methods known in the art may be used to measure the amount of histamine release from basophils from an antigen-sensitized individual in response to ISS-antigen conjugate. For example, as described herein, the amount of histamine released into the cell culture supernatant may be determined after leukocytes from blood of allergic individuals are treated with varying concentrations and/or preparations of ISS-allergen conjugates.

Methods known in the art may be used to determine the cytokine production profiles generated in response to administration of ISS-antigen conjugates. For example, the supernatants of cells treated with ISS-conjugates in vitro are analyzed for the presence of cytokines. The types and amounts of cytokines produced by lymphocytes exposed to ISS-antigen conjugates may be measured using standard ELISA format assays. A cytokine profile produced in response to an ISS-antigen conjugate may also be determined using standard cytokine bioassays including, but not limited to, those in which cell survival is dependent on the presence of a particular cytokine (for example, IL-2) and those in which a particular cytokine (for example, interferon) inhibits viral replication.

A class of conjugate may also be characterized by the extent of antigen-specific antibody suppression after administration or relative to administration of antigen alone. For example, levels of serum antibodies may be determined before and after administration of the ISS-antigen conjugate and/or antigen alone. The antibody levels at various time points may then be compared to determine the extent of antibody suppression.

A class of conjugate may also be characterized by the extent of antibody response, preferably an antigen-specific antibody response, especially an IgG response. As noted above, a class may be characterized by a ratio of (i) IgG antibodies produced in response to conjugate to (ii) IgG antibodies produced in response to antigen alone. For these characterizations and embodiments, the ratio may be (i) the sum of Th1-associated antibodies and Th2-associated antibodies elicited by ISS-antigen conjugate to (ii) the sum of Th1-associated antibodies and Th2-associated antibodies elicited antigen;

(ii) (i) a Th1-associated antibody (or antibodies) elicited by ISS-antigen conjugate to (ii) Th-1 associated antibodies elicited by antigen;

(iii) (i) a Th2-associated antibody (or antibodies) elicited by ISS-antigen conjugate to (ii) Th2-associated antibodies elicited by antigen.

A Th1-associated antibody is an antibody associated with a Th1 response. In mice, for example, IgG2a is associated with a Th1 response. In humans, IgG1 and/or IgG3 antibodies appear to be associated with a Th1 response. See, e.g., Widhe et al. (1998) Scand. J. Immunol. 47:575–581 and de Martino et al. (1999) Ann. Allergy Asthma Immunol. 83:160–164. Similarly, a Th2-associated antibody is an antibody associated with a Th2 response. In mice, IgG1 is associated with a Th2 response. In humans, IgG2 and/or IgG4 appear to be associated with a Th2 response (Widhe et al. (1998) and de Martino et al. (1999)). In both humans and mice, IgE is associated with a Th2 response. It is understood that, for these characterizations and embodiments, any one or more type of antibody may be evaluated, as long as the same antibody or antibody production level is compared to that elicited by antigen alone.

One way to calculate this ratio is in terms of amount of antibody (or antibodies) of interest produced per unit mass of conjugate versus amount of same antibody (or antibodies) produced per unit mass of antigen. The unit mass of the conjugate may be in terms of mass of antigen component of conjugate, polynucleotide component of conjugate, and/or mass of conjugate. For example, if a conjugate has a total molecular weight of 100, with the antigen component accounting for 80 and the ISS component accounting for 20, the unit mass for purposes of calculating and comparing levels of antibody production may be any of 100, 80, or 20. The Examples provide calculations in which the mass of the antigen component of the conjugate (Amb a 1) serves as the basis for calculating and comparing levels of antigen production compared to antigen alone.

Further, in calculating the ratio of antibody produced by conjugate versus antibody produced by antigen, mass of conjugate to mass of antigen may or may not be 1:1. For example, in some embodiments, antibody produced by unit mass of conjugate is compared to antibody produced by any of 2, 3, 4, 5, 6, 7, 8, 10, 15, 20, 25, 30, 40 times the mass of antigen. For example, in the case of Amb a 1, antibody produced by 1 μg of conjugate (as measured by the amount of antigen; thus 1 μg of antigen in the conjugate) is compared to antibody produced by 10 μg of Amb a 1.

ISS

In accordance with the present invention, the immunomodulatory polynucleotide contains at least one ISS, and can contain multiple ISSs. The ISSs can be adjacent within the polynucleotide, or they can be separated by additional nucleotide bases within the polynucleotide.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) Nature 374:546–549; Yamamoto et al. (1992a); Ballas et al. (1996); Klinman et al. (1997); Sato et al. (1996); Pisetsky (1996a); Shimada et al. (1986) Jpn. J. Cancer Res. 77:808–816; Cowdery et al. (1996) J. Immunol. 156:4570–4575; Roman et al. (1997); and Lipford et al. (1997a).

The ISS can be of any length greater than 6 bases or base pairs and generally comprises the sequence 5'-cytosine, guanine-3', more particularly comprises the sequence 5'-purine, purine, C, G, pyrimidine, pyrimidine-3' (such as 5'-AACGTT-3'), preferably greater than 15 bases or base pairs, more preferably greater than 20 bases or base pairs in length. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may also comprise the sequence 5'-T, C, G-3'.

In some embodiments, the ISS comprises any of the following sequences: GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG; AACGTTCG; AACGCTCG; GGCGTTCG; GGCGCTCG; GGCGTCCG; GGCGCCCG.

In some embodiments, the ISS comprises any of the following sequences: GACGCT; GACGTC; GACGTT; GACGCC; GACGCU; GACGUC; GACGUU; GACGUT; GACGTU; AGCGTT; AGCGCT; AGCGTC; AGCGCC; AGCGUU; AGCGCU; AGCGUC; AGCGUT; AGCGTU; AACGTC; AACGCC; AACGTT; AACGCT; AACGUC; AACGUU; AACGCU; AACGUT; AACGTU; GGCGTT; GGCGCT; GGCGTC; GGCGCC; GGCGUU; GGCGCU; GGCGUC; GGCGUT; GGCGTU.

In some embodiments, the immunomodulatory polynucleotide comprises the sequence 5'-TGACTGTGAACGT-TCGAGATGA-3' (SEQ ID NO:1). In other embodiments, the ISS comprises any of the sequences: 5'-TGACCGT-GAACGTTCGAGATGA-3' (SEQ ID NO:2); 5'-TCATCTC-GAACGTTCCACAGTCA-3' (SEQ ID NO:3); 5'-TGACT-GTGAACGTTCCAGATGA-3' (SEQ ID NO:4); 5'-TCCATAACGTTCGCCTAACGTTCGTC-3' (SEQ ID NO:5); 5'-TGACTGTGAABGTTCCAGATGA-3' (SEQ ID NO:6), where B is 5-bromocytosine; 5'-TGACTGTGAAB-GTTCGAGATGA-3' (SEQ ID NO:7), where B is 5-bromocytosine and 5'-TGACTGTGAABGTTBGAGATGA-3' (SEQ ID NO:8), where B is 5-bromocytosine.

An ISS and/or ISS-containing polynucleotide may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the hexameric motif described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025–2029; and Wang et al. (1994) *Nucleic Acids Res.* 22:2326–2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in *Protocols for Oliognucleotides and Analogs, Synthesis and Properties* (Agrawal, ed.) Humana Press, Totowa, N.J.; Warner et al. (1984) *DNA* 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in *Oligonucleotides as Therapeutic Agents*, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail.

Peyrottes et al. (1996) *Nucleic Acids Res.* 24:1841–1848; Chaturvedi et al. (1996) *Nucleic Acids Res.* 24:2318–2323; and Schultz et al. (1996) *Nucleic Acids Res.* 24:2966–2973. For example, synthesis of phosphorothioate oligonucleotides is similar to that described above for naturally occurring oligonucleotides except that the oxidation step is replaced by a sulfirization step (Zon (1993) "Oliognucleoside Phosphorothioates" in *Protocols for Oliognucleotides and Analogs, Synthesis and Properties* (Agrawal, ed.) Humana Press, pp. 165–190). Similarly the synthesis of other phosphate analogs, such as phosphotriester (Miller et al. (1971) *JACS* 93:6657–6665), non-bridging phosphoramidates (Jager et al. (1988) *Biochem.* 27:7247–7246), N3' to P5' phosphoramidiates (Nelson et al. (1997) *JOC* 62:7278–7287) and phosphorodithioates (U.S. Pat. No. 5,453,496) has also been described. Other non-phosphorous based modified oligonucleotides can also be used (Stirchak et al. (1989) *Nucleic Acids Res.* 17:6129–6141). Oligonucleotides with phosphorothioate backbones can be more immunogenic than those with phosphodiester backbones and appear to be more resistant to degradation after injection into the host. Braun et al. (1988) *J. Immunol.* 141:2084–2089; and Latimer et al. (1995) *Mol. Immunol.* 32:1057–1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-O-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrrolo[2,3-d]pyrimidin-5-yl, 2-amino-4-oxopyrrolo[2,3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base as described, for example, in the commonly owned application U.S. Ser. No. 09/324,191 and international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified oligonucleotides using said base-modified nucleosides as precursors, has been described, for example, in U.S. Pat. Nos. 4,910,300, 4,948,882, and 5,093, 232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000.

Antigen

Any antigen may be used in the conjugate populations of the invention.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229–1236), major dust mite allergens Der pI and Der PII (Chua et al. (1988) *J. Exp. Med.* 167:175–182; Chua et al. (1990) *Int. Arch. Allergy Appl. Immunol.* 91:124–129), white birch pollen Bet vl (Breiteneder et al. (1989) *EMBO J.* 8:1935–1938), domestic cat allergen Fel d I (Rogers et al. (1993) *Mol. Immunol.* 30:559–568), and protein antigens from tree pollen (Elsayed et al. (1991) *Scand. J. Clin. Lab. Invest. Suppl.* 204:17–31). As indicated, allergens from trees are known, including allergens from birch, juniper and Japanese cedar. Preparation of protein antigens from grass pollen for in vivo administration has been reported. Malley (1989) *J. Reprod. Immunol.* 16:173–186. As Table 1 indicates, in some embodiments, the allergen is a food allergen such as peanut allergen, for example Ara h I, and in some embodiments, the allergen is a grass allergen such as a rye allergen, for example Lol p 1. Table 1 shows a list of allergens that may be used.

TABLE 1

RECOMBINANT ALLERGENS

| Group | Allergen | Reference |
|---|---|---|
| ANIMALS: CRUSTACEA | | |
| Shrimp/lobster | tropomyosin | Leung et al. J. Allergy Clin. Immunol., 1996, 98:954–961 |
| | Pan s I | Leung et al. Mol. Mar. Biol. Biotechnol., 1998, 7:12–20 |
| INSECTS | | |
| Ant | Sol i 2 (venom) | Schmidt et al. J Allergy Clin Immunol., 1996, 98:82–8 |
| Bee | phospholipase A2 (PLA) | Muller et al. J Allergy Clin Immunol, 1995, 96:395–402 |
| | | Forster et al. J Allergy Clin Immunol, 1995, 95:1229–35 |
| | | Muller et al. Clin Exp Allergy, 1997, 27:915–20 |
| | Hyaluronidase (Hya) | Soldatova et al. J Allergy Clin Immunol, 1998, 101:691–8 |
| Cockroach | Bla g Bd9OK | Helm et al. J Allergy Clin Immunol, 1996, 98:172–80 |
| | Bla g 4 (a calycin) | Vailes et al. J Allergy Clin Immunol, 1998, 101:274–80 |
| | glutathione S-transferase | Arruda et al. J Biol Chem, 1997, 272:20907–12 |
| | Per a 3 | Wu et al. Mol Immunol, 1997, 34:1–8 |
| Dust mite | Der p 2 (major allergen) | Lynch et al. J Allergy Clin Immunol, 1998, 101:562–4 |
| | | Hakkaart et al. Clin Exp Allergy, 1998, 28:169–74 |
| | | Hakkaart et al. Clin Exp Allergy, 1998, 28:45–52 |
| | | Hakkaart et al. Int Arch Allergy Immunol, 1998, 115 (2):150–6 |
| | | Mueller et al. J Biol Chem, 1997, 272:26893–8 |
| | Der p 2 variant | Smith et al. J Allergy Clin Immunol, 1998, 101:423–5 |
| | Der f 2 | Yasue et al. Clin Exp Immunol, 1998, 113:1–9 |
| | | Yasue et al. Cell Immunol, 1997, 181:30–7 |
| | Der p 10 | Asturias et al. Biochim Biophys Acta, 1998, 1397:27–30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22:303–13 |
| Mosquito | Aed a I (salivary apyrase) | Xu et al. Int Arch Allergy Immunol, 1998, 115:245–51 |
| Yellow jacket | antigen 5, hyaluronidase, and phospholipase (venom) | King et al. J Allergy Clin Immunol, 1996, 98:588–600 |
| MAMMALS | | |
| Cat | Fel d I | Slunt et al. J Allergy Clin Immunol, 1995, 95:1221–8 |
| | | Hoffmann et al. J Allergy Clin Immunol, 1997, 99:227–32 |
| | | Hedlin Curr Opin Pediatr, 1995, 7:676–82 |
| Cow | Bos d 2 (dander; a lipocalin) | Zeiler et al. J Allergy Clin Immunol, 1997, 100:721–7 |
| | | Rautiainen et al. Biochem Bioph. Res Comm., 1998, 247:746–50 |
| | β-lactoglobulin (BLG, major cow milk allergen) | Chatel et al. Mol Immunol, 1996, 33:1113–8 |
| | | Lehrer et al. Crit Rev Food Sci Nutr, 1996, 36:553–64 |
| Dog | Can f I and Can f 2, salivary lipocalins | Konieczny et al. Immunology, 1997, 92:577–86 |
| | | Spitzauer et al. J Allergy Clin Immunol, 1994, 93:614–27 |
| | | Vrtala et al. J Immunol, 1998, 160:6137–44 |
| Horse | Equ c 1 (major allergen, a lipocalin) | Gregoire et al. J Biol Chem, 1996, 271:32951–9 |
| Mouse | mouse urinary protein (MUP) | Konieczny et al. Immunology, 1997, 92:577–86 |
| OTHER MAMMALIAN ALLERGENS | | |
| Insulin | | Ganz et al. J Allergy Clin Immunol, 1990, 86:45–51 |
| | | Grammer et al. J Lab Clin Med, 1987, 109:141–6 |
| | | Gonzalo et al. Allergy, 1998, 53:106–7 |
| Interferons | interferon alpha 2c | Detmar et al. Contact Dermatis, 1989, 20:149–50 |
| MOLLUSCS | topomyosin | Leung et al. J Allergy Clin Immunol, 1996, 98:954–61 |
| PLANT ALLERGENS: | | |
| Barley | Hor v 9 | Astwood et al. Adv Exp Med Biol, 1996, 409:269–77 |
| Birch | pollen allergen, Bet v 4 | Twardosz et al. Biochem Bioph. Res Comm., 1997, 239:197 |
| | rBet v 1 Bet v 2: (profilin) | Pauli et al. J Allergy Clin Immunol, 1996, 97:1100–9 |
| | | van Neerven et al. Clin Exp Allergy, 1998, 28:423–33 |
| | | Jahn-Schmid et al. Immunotechnology, 1996, 2:103–13 |
| | | Breitwieser et al. Biotechniques, 1996, 21:918–25 |
| | | Fuchs et al. J Allergy Clin Immunol, 1997, 100:3 56–64 |
| Brazil nut | globulin | Bartolome et al. Allergol Immunopathol, 1997, 25:135–44 |
| Cherry | Pru a I (major allergen) | Scheurer et al. Mol Immunol, 1997, 34:619–29 |
| Corn | Zm13 (pollen) | Heiss et al. FEBS Lett, 1996, 381:217–21 |
| | | Lehrer et al. Int Arch Allergy Immunol, 1997, 113:122–4 |
| Grass | Phl p 1, Phl p 2, Phl p 5 (timothy grass pollen) | Bufe et al. Am J Respir Crit Care Med, 1998, 157:1269–76 |
| | | Vrtala et al. J Immunol Jun. 15, 1998, 160:6137–44 |
| | | Niederberger et al. J Allergy Clin Immun., 1998, 101:258–64 |
| | Hol 1 5 velvet grass pollen | Schramm et al. Eur J Biochem, 1998, 252:200–6 |
| | Bluegrass allergen | Zhang et al. J Immunol, 1993, 151:791–9 |
| | Cyn d 7 Bermuda grass | Smith et al. Int Arch Allergy Immunol, 1997, 114:265–71 |
| | Cyn d 12 (a profilin) | Asturias et al. Clin Exp Allergy, 1997, 27:1307–13 |
| | | Fuchs et al. J Allergy Clin Immunol, 1997, 100:356–64 |
| Juniper | Jun o 2 (pollen) | Tinghino et al. J Allergy Clin Immunol, 1998, 101:772–7 |
| Latex | Hev b 7 | Sowka et al. Eur J Biochem, 1998, 255:213–9 |
| | | Fuchs et al. J Allergy Clin Immunol, 1997, 100:356–64 |

TABLE 1-continued

RECOMBINANT ALLERGENS

| Group | Allergen | Reference |
|---|---|---|
| Mercurialis | Mer a I (profilin) | Vallverdu et al. J Allergy Clin Immunol, 1998, 101:363–70 |
| Mustard (Yellow) | Sin a I (seed) | Gonzalez de la Pena et al. Biochem Bioph. Res Comm., 1993, 190:648–53 |
| Oilseed rape | Bra r I pollen allergen | Smith et al. Int Arch Allergy Immunol, 1997, 114:265–71 |
| Peanut | Ara h I | Stanley et al. Adv Exp Med Biol, 1996, 409:213–6<br>Burks et al. J Clin Invest, 1995, 96:1715–21<br>Burks et al. Int Arch Allergy Immunol, 1995, 107:248–50 |
| Poa pratensis | Poa p 9 | Parronchi et al. Eur J Immunol, 1996, 26:697–703<br>Astwood et al. Adv Exp Med Biol, 1996, 409:269–77 |
| Ragweed | Amb a I | Sun et al. Biotechnology August, 1995, 13:779–86<br>Hirschwehr et al. J Allergy Clin Immunol, 1998, 101:196–206<br>Casale et al. J Allergy Clin Immunol, 1997, 100:110–21 |
| Rye | Lol p I | Tamborini et al. Eur J Biochem, 1997, 249:886–94 |
| Walnut | Jug r I | Teuber et al. J Allergy Clin Immun., 1998, 101:807–14 |
| Wheat | allergen | Fuchs et al. J Allergy Clin Immunol, 1997, 100:356–64<br>Donovan et al. Electrophoresis, 1993, 14:917–22 |
| FUNGI: | | |
| *Aspergillus* | Asp f 1, Asp f 2, Asp f 3, Asp f 4, rAsp f 6 | Crameri et al. Mycoses, 1998, 41 Suppl 1:56–60<br>Hemmann et al. Eur J Immunol, 1998, 28:1155–60<br>Banerjee et al. J Allergy Clin Immunol, 1997, 99:821–7<br>Crameri Int Arch Allergy Immunol, 1998, 115:99–114<br>Crameri et al. Adv Exp Med Biol, 1996, 409:111–6<br>Moser et al. J Allergy Clin Immunol, 1994, 93:1–11 |
| | Manganese superoxide dismutase (MNSOD) | Mayer et al. Int Arch Allergy Immunol, 1997, 113:213–5 |
| *Blomia* | allergen | Caraballo et al. Adv Exp Med Biol, 1996, 409:81–3 |
| *Penicillinium* | allergen | Shen et al. Clin Exp Allergy, 1997, 27:682–90 |
| *Psilocybe* | Psi c 2 | Horner et al. Int Arch Allergy Immunol, 1995, 107:298–300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, core proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein. References discussing influenza vaccination include Scherle and Gerhard (1988) *Proc. Natl. Acad. Sci. USA* 85:4446–4450; Scherle and Gerhard (1986) *J. Exp. Med.* 164:1114–1128; Granoff et al. (1993) *Vaccine* 11:S46–51; Kodihalli et al. (1997) *J. Virol.* 71:3391–3396; Ahmeida et al. (1993) *Vaccine* 11:1302–1309; Chen et al. (1999) *Vaccine* 17:653–659; Govorkova and Smirnov (1997) *Acta Virol.* (1997) 41:251–257; Koide et al. (1995) *Vaccine* 13:3–5; Mbawuike et al. (1994) *Vaccine* 12:1340–1348; Tamura et al. (1994) *Vaccine* 12:310–316; Tamura et al. (1992) *Eur. J. Immunol.* 22:477–481; Hirabayashi et al. (1990) *Vaccine* 8:595–599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX® II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, microorganisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833–839. Proteolytic enzymes can also be utilized to couple amino acids to produce peptides. Kullmann (1987) *Enzymatic Peptide Synthesis*, CRC Press, Inc. Alternatively, the peptide can be obtained by using the biochemical machinery of a cell, or by isolation from a biological source. Recombinant DNA techniques can be employed for the production of peptides. Hames et al.

(1987) *Transcription and Translation: A Practical Approach*, IRL Press. Peptides can also be isolated using standard techniques such as affinity chromatography.

Preferably the antigens are peptides, lipids (e.g., sterols, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see *Human Retroviruses and AIDS Compendium* (for example, 1998 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

ISS-Antigen Conjugation

In compositions described herein, the ISS-containing polynucleotide is conjugated with the antigen. The ISS portion can be coupled with the antigen portion of a conjugate in a variety of ways, including covalent and/or non-covalent interactions.

The link between the portions can be made at the 3' or 5' end of the ISS, or at a suitably modified base at an internal position in the ISS. If the antigen is a peptide and contains a suitable reactive group (e.g., an N-hydroxysuccinimide ester) it can be reacted directly with the $N^4$ amino group of cytosine residues. Depending on the number and location of cytosine residues in the ISS, specific coupling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the antigen of interest.

Where the antigen is a peptide, this portion of the conjugate can be attached to the 3'-end of the ISS through solid support chemistry. For example, the ISS portion can be added to a polypeptide portion that has been pre-synthesized on a support. Haralambidis et al. (1990a) *Nucleic Acids Res.* 18:493–499; and Haralambidis et al. (1990b) *Nucleic Acids Res.* 18:501–505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) *Nucleic Acids Res.* 15:5305–5321; and Corey et al. (1987) *Science* 238:1401–1403) or a terminal amino group is left at the 3'-end of the oligonucleotide (Nelson et al. (1989) *Nucleic Acids Res.* 17:1781–1794). Conjugation of the amino-modified ISS to amino groups of the peptide can be performed as described in Benoit et al. (1987) *Neuromethods* 6:43–72. Conjugation of the thiol-modified ISS to carboxyl groups of the peptide can be performed as described in Sinha et al. (1991), pp. 185–210, *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464–465.

The peptide portion of the conjugate can be attached to the 5'-end of the ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227–6245; Connolly (1985) *Nucleic Acids Res.* 13:4485–4502; Kremsky et al. (1987) *Nucleic Acids Res.* 15:2891–2909; Connolly (1987) *Nucleic Acids Res.* 15:3131–3139; Bischoff et al. (1987) *Anal. Biochem.* 164:336–344; Blanks et al. (1988) *Nucleic Acids Res.* 16:10283–10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinha et al. (1991).

An ISS-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643–7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between ISS and antigens can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugates (Yanagawa et al. (1988) *Nucleic Acids Symp. Ser.* 19:189–192), oligonucleotide-fatty acid conjugates (Grabarek et al. (1990) *Anal. Biochem.* 185:131–135; and Staros et al. (1986) *Anal. Biochem.* 156:220–222), and oligonucleotide-sterol conjugates. Boujrad et al. (1993) *Proc. Natl. Acad. Sci. USA* 90:5728–5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J Applied Biochem.* 7:347–355.

The linkage of a circular ISS to a peptide or antigen can be formed in several ways. Where the circular ISS is synthesized using recombinant or chemical methods, a modified nucleoside is suitable. Ruth (1991), pp. 255–282, in *Oligonucleotides and Analogues: A Practical Approach*, IRL Press. Standard linking technology can then be used to connect the circular ISS to the antigen or other peptide. Goodchild (1990) *Bioconjug. Chem.* 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138–146.

Compositions and Kits Comprising the Conjugate Populations

The present invention also provides kits and compositions, such as pharmaceutical formulations, which comprise any of the conjugate populations described herein.

Kits of the invention comprise any of the conjugate populations described herein in suitable packaging. The kits of the invention may optionally contain instructions for their use (for example, instructions for any of the methods described herein) and/or any other suitable components.

The compositions of the invention, especially useful to administering to an individual in need of immune modulation (in the context of, for example, infectious disease, cancer, and allergy) generally comprise any of the conjugate populations described herein in a sufficient amount to modulate an immune response.

Generally, the compositions of the invention preferably also comprise a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonperenteral drug delivery are set forth in *Remington's Pharmaceutical Sciences* 19th Ed. Mack Publishing (1995).

Other formulations include suitable delivery forms known in the art including, but not limited to, carriers such as liposomes. Mahato et al. (1997) *Pharm. Res.* 14:853–859. Liposomal preparations include, but are not limited to, cytofectins, multilamellar vesicles and unilamellar vesicles.

Generally, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

Other formulations include suitable delivery forms known in the art including, but not limited to, carriers such as liposomes, Mahato et al. (1997) *Pharm. Res.* 14:853–859. Liposomal preparations include, but are not limited to, cytofectins, multilamellar vesicles and unilamellar vesicles.

In some embodiments, more than one antigen(s) may be present in a composition. Such compositions may contain at least one, at least two, at least three, at least four, at least five different antigen(s). Such "cocktails", as they are often denoted in the art, may be particularly useful in treating individuals who, for example, are allergic to more than one allergen.

The invention also includes a formulation for use in allergy immunotherapy, comprising a pharmaceutically acceptable excipient and a population of conjugate molecules, said conjugate molecules comprising an antigen which is an allergen and one or more ISS-containing polynucleotides, wherein said population suppresses histamine release from basophils from an individual sensitized to the antigen as compared to histamine release induced by the antigen. The extent of suppression of histamine release may be any described herein. In some embodiments, the allergen is Amb a 1.

Generally, the efficacy of administering any of these compositions is adjusted by measuring any change in the immune response as described herein, or other clinical parameters.

The invention provides for compositions which comprise any ISS-antigen conjugate population described herein and an adjuvant where, upon co-administration, the association of ISS-antigen and adjuvant is effective to enhance an immune response compared to the co-administration of the ISS-antigen without adjuvant. In such compositions, the adjuvant is maintained in association with ISS-antigen so as to recruit and activate target cells to the ISS-antigen. Targets of the ISS-antigen conjugate include, but are not limited to, antigen presenting cells (APCs), such as macrophages, dendritic cells, and/or lymphocytes, lymphatic structures, such as lymph nodes and/or the spleen, and nonlymphatic structures, particularly those in which dendritic cells are found, such as skin, lungs, and/or gastrointestinal tract.

In some embodiments, the invention provides compositions comprising ISS-antigen conjugate populations as described herein and an adjuvant whereby the ISS/antigen/adjuvant are co-administered. Preferably, the immunogenic composition contains an amount of an adjuvant sufficient to potentiate the immune response to the immunogen. Adjuvants are known in the art and include, but are not limited to, oil-in-water emulsions, water-in oil emulsions, alum (aluminum salts), liposomes and microparticles including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875, as well as, lipid-based adjuvants and others described herein. For veterinary use and for production of antibodies in animals, mitogenic components of Freund's adjuvant (both complete and incomplete) can be used. In some embodiments, the ISS-antigen conjugate can be associated with an adjuvant through covalent and/or non-covalent interactions. An example of such non-covalent interactions includes, but is not limited to, adsorption of the ISS and antigen to microparticles described herein.

In some embodiments, the ISS-antigen populations described herein can be administered in conjunction with one or more immunomodulatory facilitators. Thus, the invention provides compositions comprising ISS-antigen conjugate populations and an immunomodulatory facilitator. As used herein, the term "immunomodulatory facilitator" refers to molecules which support and/or enhance the immunomodulatory activity of an ISS. Examples of immunomodulatory facilitators can include co-stimulatory molecules, such as cytokines, and/or adjuvants. The association of the ISS and the facilitator molecules in an ISS-facilitator conjugate can be through covalent interactions and/or through non-covalent interactions, including high affinity and/or low affinity interactions. Examples of non-covalent interactions that can couple an ISS and a facilitator in an ISS-facilitator conjugate include, but are not limited to, ionic bonds, hydrophobic interactions, hydrogen bonds and van der Waals attractions.

Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with ISS are the interleukins (e.g., IL-1, IL-2, IL-3, etc.), interferons (e.g., IFN-$\alpha$, IFN-$\beta$, IFN-$\gamma$), erythropoietin, colony stimulating factors (e.g., G-CSF, M-CSF, GM-CSF) and TNF-$\alpha$. Preferably, immunostimulatory peptides for use in conjunction with ISS oligonucleotides are those that stimulate Th1-type immune responses, such as IL-12 (Bliss et al. (1996) *J. Immunol.* 156:887–894), IL-18, TNF-$\alpha$, $\beta$ and $\gamma$, and/or transforming growth factor (TGF)-$\alpha$.

Peptides administered with ISS can also include amino acid sequences that mediate protein binding to a specific receptor or that mediate targeting to a specific cell type or tissue. Examples include, but are not limited to, antibodies or antibody fragments, peptide hormones such as human growth hormone, and enzymes. Immunomodulatory peptides also include peptide hormones, peptide neurotransmitters and peptide growth factors. Co-stimulatory molecules such as B7 (CD80), trans-activating proteins such as transcription factors, chemokines such as macrophage chemotactic protein (MCP) and other chemoattractant or chemotactic peptides are also useful peptides for administration with ISS.

The invention also provides compositions which comprise and ISS-antigen conjugate in conjunction with colloidal dispersion systems, such as microspheres, beads, macromolecular complexes, nanocapsules and lipid-based system, such as oil-in-water emulsions, micelles, mixed micelles and liposomes. Colloidal dispersion systems can provide effective encapsulation of ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809–1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing ISS-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715–724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

Administration and Assessment of the Immune Response

The ISS-containing polynucleotide-antigen conjugate can be administered in combination with other pharmaceutical and/or immunogenic and/or immunostimulatory agents and can be combined with a physiologically acceptable carrier thereof.

The ISS-containing polynucleotide may be any of those described above. As indicated in SEQ ID NO:1, preferably, the ISS-containing polynucleotide administered comprises the sequence 5'-T, C, G-3'. Preferably, the ISS-containing polynucleotide administered comprises the formula 5' purine, purine, C, G, pyrimidine, pyrimidine, C, G-3'; more preferably, 5'-A, A, C, G, T, T, C, G-3'. Another preferred embodiment uses SEQ ID NO:1.

As with all immunogenic compositions, the immunologically effective amounts and method of administration of the particular ISS-antigen formulation can vary based on the individual, what condition is to be treated and other factors evident to one skilled in the art. Factors to be considered include the antigenicity, whether or not ISS-antigen conjugate will be complexed with or covalently attached to an adjuvant or delivery molecule, route of administration and the number of immunizing doses to be administered. Such factors are known in the art and it is well within the skill of immunologists to make such determinations without undue experimentation. A suitable dosage range is one that provides the desired modulation of immune response to the antigen. Generally, a dosage range of the ISS-antigen composition may be, for example, from about any of the following: 01. to 100 µg, 01. to 50 µg, 01. to 25 µg, 01. to 10 µg, 1 to 500 µg, 100 to 400 µg, 200 to 300 µg, 1 to 100 µg, 100 to 200 µg, 300 to 400 µg, 400 to 500 µg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 25 µg, 50 µg and 100 µg. In these compositions, the molar ratio of ISS-containing polynucleotide to antigen may vary. The absolute amount given to each patient depends on pharmacological properties such as bioavailability, clearance rate and route of administration.

The effective amount and method of administration of the particular ISS-antigen formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient ISS-containing composition to attain a tissue concentration of about 1–10 µM as measured by blood levels. The absolute amount given to each patient depends on pharmacological properties such as bioavailability, clearance rate and route of administration.

As described herein, APCs and tissues with high concentration of APCs are preferred targets for the ISS and antigen-containing compositions. Thus, administration of ISS and antigen-containing compositions to mammalian skin and/or mucosa, where APCs are present in relatively high concentration, is preferred.

The present invention provides ISS-antigen-containing compositions suitable for topical application including, but not limited to, physiologically acceptable implants, ointments, creams, rinses and gels. Topical administration is, for instance, by a dressing or bandage having dispersed therein a delivery system, or by direct administration of a delivery system into incisions or open wounds. Creams, rinses, gels or ointments having dispersed therein an ISS/antigen-containing composition are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the ISS/antigen-containing composition to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LEC- TRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850–853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up ISS/antigen-containing compositions transferred from the end of the tines. For example, the MONO-VACC old tuberculin test manufactured by Pasteur Merieux of Lyon, France contains a device suitable for introduction of ISS/antigen-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of ISS/antigen-containing composition. Use of the device is preferably according to the manufacturer's written instructions included with the device product. Similar devices which can also be used in this embodiment are those which are currently used to perform allergy tests.

Another suitable approach to epidermal administration of ISS is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The ISS can be suspended in a carrier which also contains the chemical irritant or coadministered therewith.

Another delivery method for administering ISS/antigen-containing compositions makes use of non-lipid polymers, such as a synthetic polycationic amino polymer. Leff (1997) *Bioworld* 86:1–2.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to, pharmaceutically acceptable sterile isotonic solutions. Such solutions include, but are not limited to, saline and phosphate buffered saline for injection of the ISS-containing compositions.

Gastrointestinal routes of administration include, but are not limited to, ingestion and rectal. The invention includes ISS/antigen-containing compositions suitable for gastrointestinal administration including, but not limited to, pharmaceutically acceptable, powders, pills or liquids for ingestion and suppositories for rectal administration.

Naso-pharyngeal and pulmonary routes of administration include, but are not limited to, inhalation, transbronchial and transalveolar routes. The invention includes ISS/antigen-containing compositions suitable for administration by inhalation including, but not limited to, various types of aerosols for inhalation, as well as powder forms for delivery systems. Devices suitable for administration by inhalation of ISS/antigen-containing compositions include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119–6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the ISS/antigen-containing compositions of the invention. The methods of producing the various compositions and devices are within the ability of one skilled in the art and are not described in detail here.

Analysis (both qualitative and quantitative) of the immune response to ISS/antigen-containing compositions can be by any method known in the art, including, but not limited to, measuring antigen-specific antibody production (including measuring specific antibody subclasses), activation of specific populations of lymphocytes such as $CD4^+$ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as $CD4^+$ T cells can be achieved, for example, with fluorescence-activated cell sorting (FACS). Cytotoxicity assays can be performed for instance as described in Raz et al. (1994) *Proc. Natl. Acad. Sci. USA* 91:9519–9523. Serum concentrations of cytokines can be measured, for example, by ELISA. These and other assays to evaluate the immune response to an immunogen are well known in the art. See, for example, *Selected Methods in Cellular Immunology* (1980) Mishell and Shiigi, eds., W.H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an ISS/antigen-containing composition can be determined by any method known in the art including, but not limited to: (1) a reduction in levels of IL-4 or IL-5 measured before and after antigen-challenge; or detection of lower (or even absent) levels of IL-4 or IL-5 in an ISS/antigen treated host as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an ISS/antigen treated host as compared to an antigen-primed or, primed and challenged, control treated without ISS; (3) "Th1-type biased" antibody production in an ISS/antigen treated host as compared to a control treated without ISS; and/or (4) a reduction in levels of antigen-specific IgE as measured before and after antigen challenge; or detection of lower (or even absent) levels of antigen-specific IgE in an ISS/antigen treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to ISS/antigen treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th-1 associated antibodies may be measured. Examples of such Th1-type biased antibodies include, but are not limited to, human IgG1 and/or IgG3 (see, e.g., Widhe et al. (1998) Scand. J. Immunol. 47:575–581 and de Martino et al. (1999) Ann. Allergy Asthma Immunol. 83:160–164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of ISS administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-S, as well as IgE reduction and reduction in histamine release in response to allergen.

Methods of the Invention

The invention also includes methods of modulating an immune response comprising administering a population of conjugates (typically in a composition comprising the population and a pharmaceutically acceptable excipient) such that the desired modulation of the immune response is achieved. Administration of the conjugates and assessment of immune responses have been described above.

In some embodiments, the invention provides methods of modulating an immune response in an individual which comprise administering a composition comprising any of the populations described herein to the individual in an amount sufficient to modulate the immune response. Generally, the individual is in need of, or will be in need of, such modulation, due, for example, for a disease condition or being at risk of developing a disease condition. Examples of disease conditions include, but are not limited to, allergy, cancer, infectious diseases (such as viral or bacterial infection).

In some embodiments, the immune modulation comprises stimulating a (i.e., one or more) Th1-associated cytokine, such as interferon-γ. In some embodiments, the immune modulation comprises suppressing production of a (i.e., one or more) Th2-associated cytokine, such as IL-4 and/or IL-S. Measuring these parameters uses methods standard in the art and has been discussed above.

In some embodiments, one or more Th 1-associated cytokines is produced, while antigen-specific antibody production is suppressed. Measuring these parameters uses methods standard in the art and has been discussed above.

In, one embodiment, the immune modulation comprises stimulating a (i.e., one or more) Th1-associated cytokine, such as interferon-γ, and suppressing production of antigen-specific antibodies. Degrees of suppression of antigen-specific antibody production for various conjugate populations, including Th1-associated antibody production and combination of Th1- and Th2-associated antibody production, have been described above and apply to these methods.

In some embodiments, the immune modulation comprises suppression of histamine release. Degrees of suppression of histamine release for various conjugate populations have been described above and apply to these methods.

As Examples 2–4 convey, the invention also provides methods of suppressing antibody formation, preferably antigen-specific antibody formation, in an individual, while stimulating production of a Th1-associated cytokine comprising administering a population ISS-antigen conjugate of the H class to the individual whereby antibody formation is suppressed while a Th1-associated cytokine is stimulated. Measuring these parameters uses methods standard in the art and has been discussed above.

In some embodiments, the invention provides methods of treating an allergic condition in an individual which comprise administering any of the populations described herein in which the antigen is an allergen (generally in a composition comprising such a composition and a pharmaceutically acceptable excipient) in an amount sufficient to ameliorate or palliate the allergic condition, generally by modulating the immune response to the antigen. Palliation can be determined by, for example, alleviation of one or more symptoms associated with allergy.

The invention also provides methods of reducing allergenicity of an antigen, particularly an allergen, comprising conjugating the allergen to ISS-containing polynucleotide, such that allergenicity is reduced compared to antigen alone (i.e., antigen not linked to ISS). In some embodiments, the invention provides methods of reducing allergenicity of an antigen, particularly an allergen, comprising conjugating the allergen to ISS-containing polynucleotide, whereby the average number of ISS to allergen is such that allergencity is reduced compared to a population of conjugate molecules having a lower average number of ISS to antigen. Measurement of modulation of various aspects of an immune response (including Th1 and Th2-type responses) has been described above.

In some embodiments, the invention provides methods for generating antigen-specific CTL activity while suppressing production of antigen-specific antibodies.

The invention also provides methods of making these classes of conjugates comprising any of the techniques and/or steps described herein.

The following Examples are provided to illustrate but not limit the present invention.

EXAMPLES

Example 1

Preparation of AIC-L, AIC-M, or AIC-H

Figure 12:
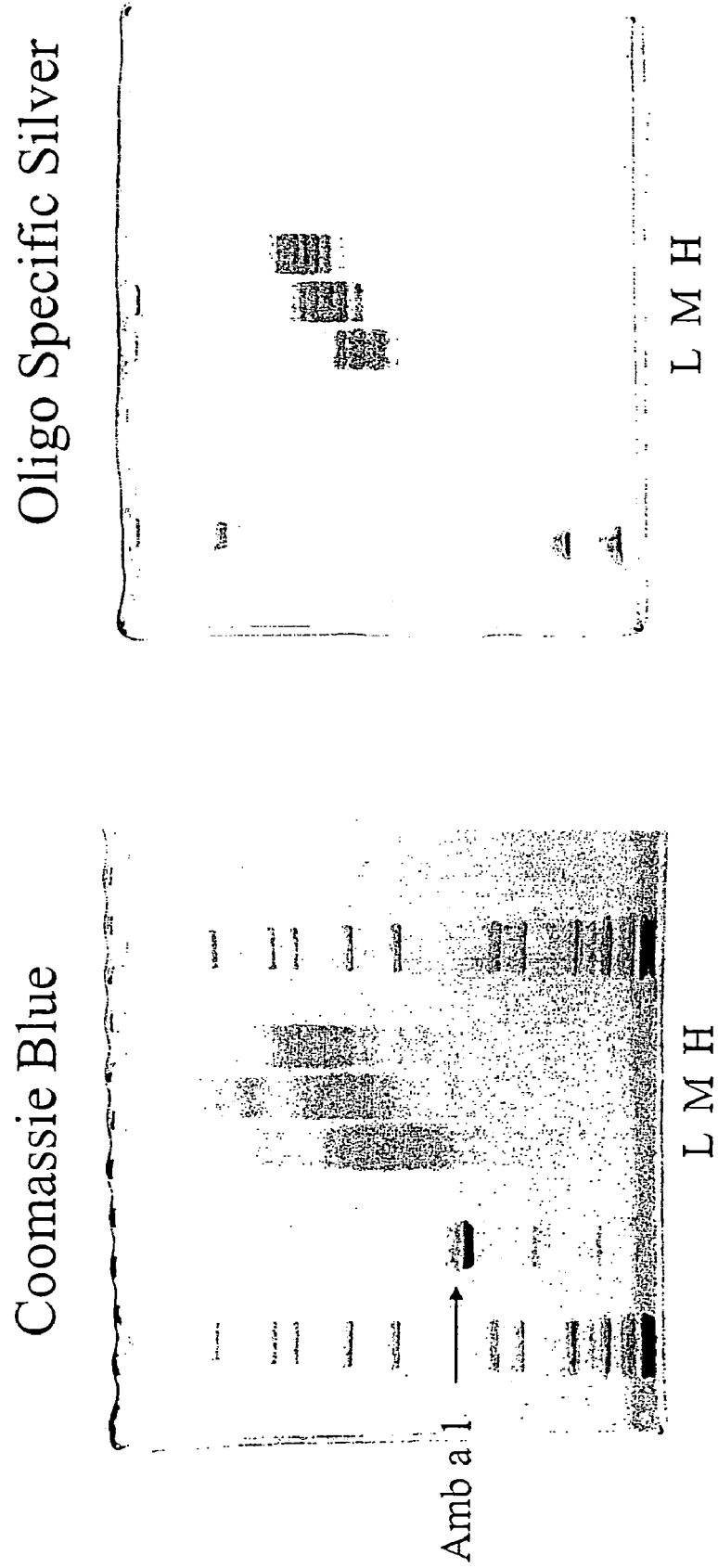
Figure 13:
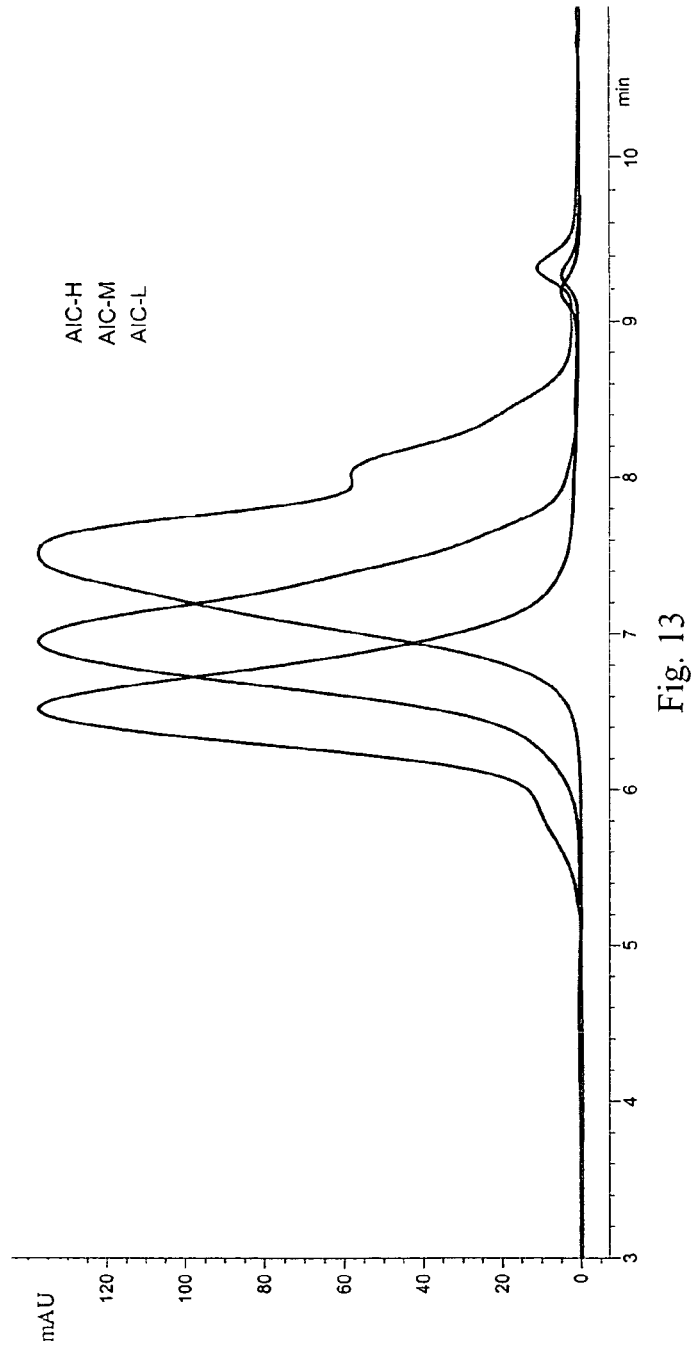
Figure 14:
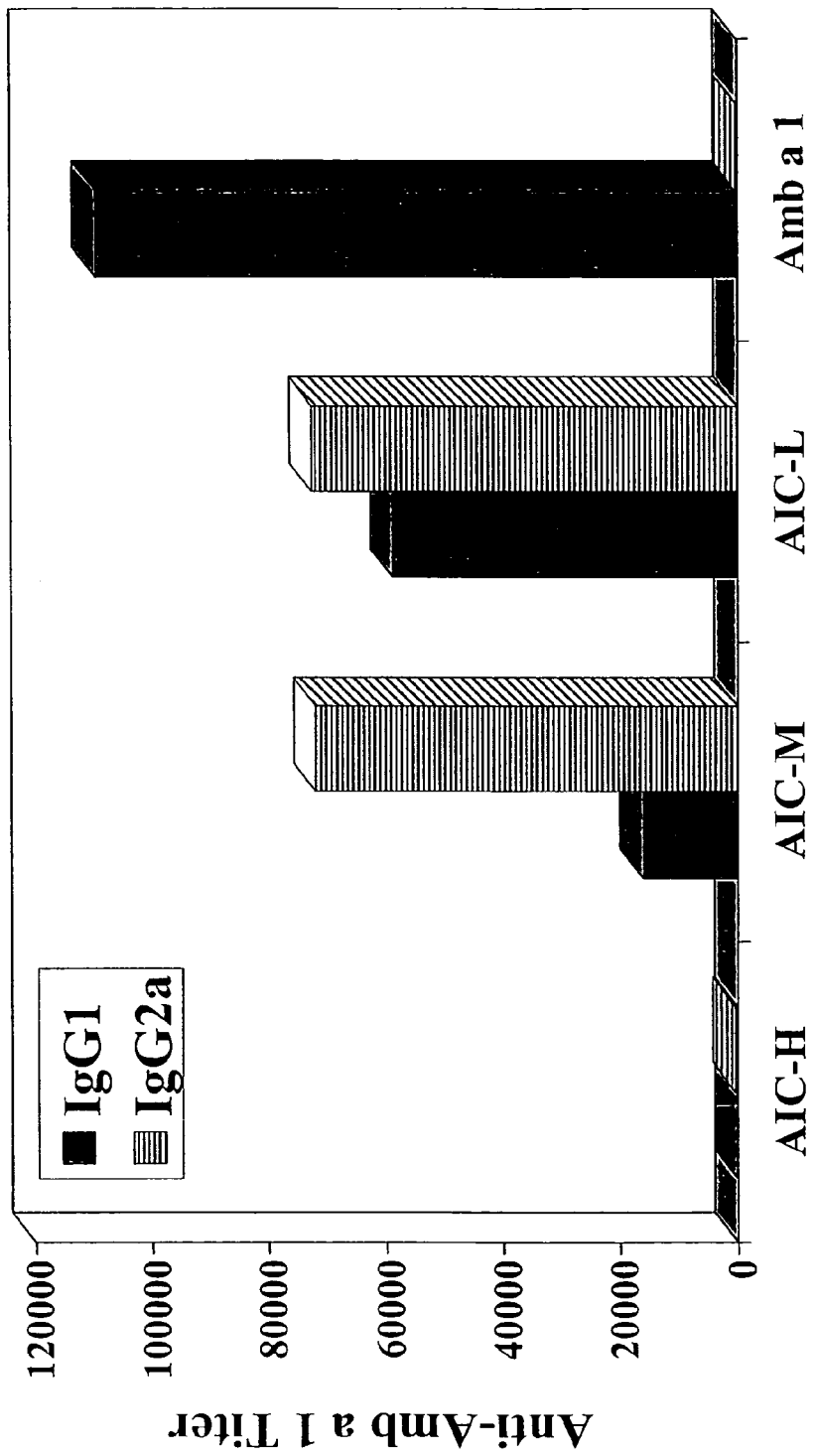
FIG. 14 is a bar graph depicting anti-Amb a 1 IgG1 (left bar) and IgG2a (right bar) production two weeks post second immunization in mice receiving AIC-H, AIC-M, and AIC-L, versus Amb a 1.
Figure 15:
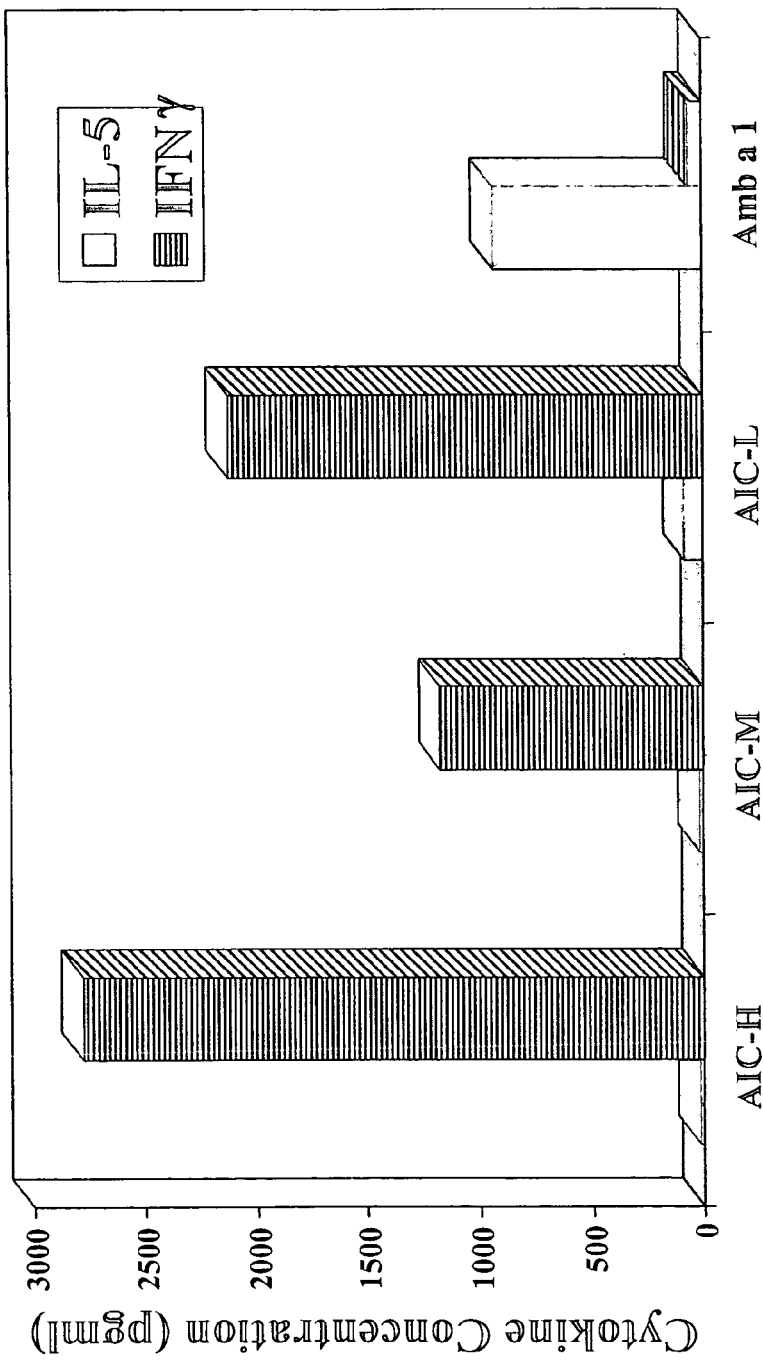
FIG. 15 is a bar graph depicting IL-5 (left bar) and interferon γ (right bar) production four weeks post second immunization in mice receiving AIC-H, AIC-M or AIC-L compared to receiving Amb a 1.

AIC-L, AIC-M, and AIC-H are covalent conjugates of the ragweed allergen Amb a 1 and the ISS-containing polynucleotide SEQ ID NO:1. All three classes of conjugate are prepared from the same ISS-containing polynucleotide and employing the same heterobifunctional linker. The number of oligonucleotides conjugated to the Amb a 1 can distinguish the classes. The amount of oligonucleotide bound to Amb a 1 can be determined by the measurement of size or the molecular weight of the conjugates (see FIGS. 12 and 13). AIC-L contains an average of 2–3 oligonucleotides per Amb a 1 molecule, AIC-M an average of 3.5 to 4.5, and AIC-H contains an average of >5.5. These three classes of AIC have different biological properties as described below.

Preparation and Isolation of 5'thio ISS Oligonucleotide

Triscarboxyethylphosphine (TCEP) was allowed to reach ambient temperature and dissolved in 10 mM $NaPO_4$/141 mM NaCl/pH 7.2. The 5' disulfide ISS oligonucleotide was allowed to reach ambient temperature, dissolved in the same buffer, and treated with the TCEP solution for 2 hours at 40° C. This material was carried on directly to the isolation step.

Two pre-packed desalting columns were connected in series and equilibrated with 10 mM $NaPO_{4/141}$ mM NaCl/pH 7.2 buffer. The 5'disulfide ISS oligonucleotide reduction mixture was loaded onto the column and the 5'thio ISS oligonucleotide was eluted isocratically.

Preparation and Isolation of Maleimide-Activated Amb a 1

N-ethyl maleimide (NEM) was allowed to reach ambient temperature and dissolved with stirring in dimethyl sulfoxide (DMSO). Amb a 1 was thawed and treated with the NEM solution for 2 hours at 20° C. Sulfosuccinimidyl-4-(N-maleimidomethyl) cyclohexane-1-carboxylate (sSMCC) was allowed to reach ambient temperature and dissolved in DMSO. The NEM blocked Amb a 1 was treated with the sSMCC solution for 2.5 hours at 20° C. This material was carried on directly to the isolation step. Two pre-packed desalting columns were connected in series and equilibrated with 10 mM $NaPO_4$/141 mM NaCl/pH 7.2 buffer. The Amb a 1 activation mixture was loaded onto the column and the maleimide activated Amb a 1 was eluted isocratically.

Preparation and Isolation of AIC-L, AIC-M or AIC-H

The crude AIC-L conjugate was prepared by incubation of a mixture of 4 molar equivalents of 5' thio ISS oligonucleotide and 1 molar equivalent the maleimide activated Amb a 1 for 3 hours at 20° C. Crude AIC-M and AIC-H were prepared in a similar manner but by addition of 7 and 17 molar equivalents of 5' thio ISS oligonucleotide respectively. A pre-packed gel filtration column was equilibrated with 10 mM $NaPO_{4/141}$ mM NaCl/pH 7.2 buffer and the crude AIC-L, AIC-M, or AIC-H were loaded onto the column. The AIC was eluted isocratically with 10 mM $NaPO_{4/141}$ mM NaCl/pH 7.2 buffer.

Example 2

AIC-H, AIC-M and AIC-L Immunogenicity in Mice

Groups of 10 BALB/c mice were immunized with 1/g AIC (H, M, or L) intradermally in the tail. Control mice receive identical injections of 10 μg Amb a 1. Mice received 2 immunizations at a two-week interval. Two weeks after the first and second immunizations, mice were bled, sera prepared, and Amb a 1-specific IgG1 and IgG2a were measured by ELISA. In the mouse system, IgG1 responses are associated with Th2-type immune responses while IgG2a responses are associated with Th1-type responses.

In some experiments, mice were sacrificed four weeks after the second immunization, spleens were harvested and spleen cell cultures were prepared. These cultures were stimulated in vitro for four days with Amb a 1 and IFNγ and IL-5 secreted into the media in response to Amb a 1 was measured by ELISA. IFNγ is a product of Th1 cells while IL-5 is a product of Th2 cells.

Comparison of Immunogenicity of AIC-L, AIC-M, and Amb a 1

The antibody response to AIC-L, AIC-M, and Amb a 1 is shown in Table 2 (mean titer±standard deviation). AIC-M induced a very low IgG1 response and a higher IgG2a response after the first immunization. After the second immunization, both the IgG1 and IgG2a responses increased with the IgG2a response remaining about five-fold higher than the IgG1 response. AIC-L induced higher IgG1 and IgG2a responses than AIC-M after both the first and second immunization. The antibody response with AIC-L was also weighted more heavily toward IgG2a responses than IgG1 responses. The antibody responses to both AIC-M and AIC-L, showing IgG2a>IgG1, are indicative of a Th1-type immune response. In contrast, unmodified Amb a 1 induced high IgG1 and low IgG2a responses after both the first and second immunization. This type of antibody responses is indicative of a Th2-type of immune response. Thus, both the AIC-L and AIC-M modifications of Amb a 1 shift the immune response of a Th2-type antigen (Amb a 1) toward a Th1 profile. AIC-L appeared to generate higher total antibody responses than AIC-M.

TABLE 2

Antibody Response to AIC-L, AIC-M, and Amb a 1

| Immunization material | Antibody response 2 weeks post 1st Immunization | | Antibody response 2 weeks post 2nd Immunization | |
|---|---|---|---|---|
| | IgG1 | IgG2a | IgG1 | IgG2a |
| AIC-M Lot BK10 | 86 ± 120 | 1326 ± 2001 | 18393 ± 18782 | 106241 ± 101353 |
| AIC-L Lot BK11 | 834 ± 623 | 3879 ± 2370 | 86201 ± 29364 | 142688 ± 57892 |
| Amb a 1 Lot 11 July 98 | 2559 ± 4193 | 20 ± 43 | 176332 ± 94876 | 1410 ± 3041 |

Comparison of Immunogenicity of AIC-L, AIC-M, and Amb a 1

A second experiment demonstrating the antibody response to AIC-L, AIC-M, and Amb a 1 is shown in Table 3 (mean titer±standard deviation). The results of this experiment are similar, but not identical to the experiment above. IgG1 responses overall were higher in this experiment than in the above experiment. Otherwise the conclusions are the same. Both the AIC-L and AIC-M modifications of Amb a 1 shift the immune response of a Th2-type antigen (Amb a 1) toward a Th1 profile. AIC-L appears to generate higher total antibody responses than AIC-M.

TABLE 3

Antibody Response to AIC-L, AIC-M, and Amb a 1

| Immunization material | Antibody response 2 weeks post 1st Immunization | | Antibody response 2 weeks post 2nd Immunization | |
|---|---|---|---|---|
| | IgG1 | IgG2a | IgG1 | IgG2a |
| AIC-M | 144 ± | 1648 ± | 25740 ± | 29584 ± |
| Lot BK10 | 161 | 1558 | 20975 | 21747 |
| AIC-L | 1028 ± | 7165 ± | 229272 ± | 276035 ± |
| Lot BK11 | 686 | 4887 | 118590 | 330059 |
| Amb a 1 | 5832 ± | 14 ± | 296417 ± | 890 ± |
| Lot 11 July 98 | 6285 | 24 | 256744 | 1100 |

Comparison of Immunogenicity of AIC-M, AIC-H, -and Amb a 1

The antibody response to AIC-M, AIC-H, and Amb a 1 is shown in Table 4 (mean titer±standard deviation). AIC-M produced an antibody response similar to the previous experiments, with IgG2a titers greater than IgG1 titers. AIC-H induces lower IgG1 and IgG2a responses than AIC-M after both the first and second immunization. The antibody response with AIC-H is also weighted more heavily toward IgG2a responses than IgG1 responses. The unmodified Amb a 1 again induced high IgG1 and low IgG2a responses after both the first and second immunization. Thus, both the AIC-H and AIC-M modifications of Amb a 1 shift the immune response of a Th2-type antigen (Amb a 1) toward a Th1 profile. AIC-H appears to generate lower total antibody responses than AIC-M.

TABLE 4

Antibody Response to AIC-M, AIC-H, and Amb a 1

| Immunization material | Antibody response 2 weeks post 1st Immunization | | Antibody response 2 weeks post 2nd Immunization | |
|---|---|---|---|---|
| | IgG1 | IgG2a | IgG1 | IgG2a |
| AIC-M | 126 ± | 1191 ± | 15456 ± | 39032 ± |
| Lot BK12 | 19 | 1725 | 7184 | 17288 |
| AIC-H | 125 ± | 281 ± | 1138 ± | 13017 ± |
| Lot BK8 | 15 | 269 | 2340 | 17925 |
| Amb a 1 | 243 ± | 120 ± | 52322 ± | 797 ± |
| Lot 03 August 98 | 265 | 0 | 58128 | 1057 |

Comparison of Immunogenicity of AIC-M, AIC-H, -and Amb a 1

This experiment (summarized in Table 5; mean titer±standard deviation) reproduces the results summarized in Table 4 and includes one additional AIC-H lot. This experiment confirms that AIC-M and AIC-H produce similar Th1 responses and that AIC-H produces lower antibody responses than AIC-M.

TABLE 5

Antibody Response to AIC-M, AIC-H, and Amb a 1

| Immunization material | Antibody response 2 weeks post 1st Immunization | | Antibody response 2 weeks post 2nd Immunization | |
|---|---|---|---|---|
| | IgG1 | IgG2a | IgG1 | IgG2a |
| AIC-M | 44 ± | 675 ± | 8345 ± | 24747 ± |
| Lot BK10 | 26 | 972 | 4366 | 28208 |
| AIC-H | <30 ± | 129 ± | 848 ± | 4332 ± |
| Lot BK8 | 0 | 224 | 2101 | 8489 |
| AIC-H | 46 ± | <30 ± | 352 ± | 2079 ± |
| Lot BK278 | 43 | 1 | 327 | 2029 |
| Amb a 1 | 5924 ± | 69 ± | 120628 ± | 776 ± |
| Lot 12 April 98 | 8342 | 108 | 106455 | 935 |

Antigen-specific antibody responses to immunizations with AIC-L, AIC-M and AIC-H compared to those responses to immunization with Amb a 1 are also depicted in FIGS. 4, 7 and 14. These results indicate that immunization with AIC-H results in lower antigen-specific antibody responses than immunization with AIC-M or with AIC-L.

Th2 to Th1 Shift in Immune Response with AIC-H

Mice were primed at week 0 with Amb a 1 in alum which generated a Th2 response. At week 15, these mice were treated with 3 injections two weeks apart with 10 μg each of Amb a 1 or AIC-H (lot BK 5) (see FIGS. 1–3, injections indicated by arrows). Amb a 1-specific IgG1, IgE and IgG2a were measured by ELISA and the results are depicted in FIGS. 1–3, respectively.

AIC-H treatments resulted in a shift from the Th2 response to a Th1-type response as indicated by a reduction in the amount of Amb a 1-specific IgG1 and IgE produced and an increase in the amount of Amb a 1-specific IgG2a produced. In contrast, treatment with unmodified Amb a 1 resulted in higher IgG1 and IgE responses and a lower IgG2a response.

Example 3

Th1-Associated Cytokines are Induced in Mice Immunized with AIC-M and AIC-H but not with Amb a 1 Alone Cytokine responses of spleen cells to Amb a 1 exposure in vitro are shown in Table 6 (mean titer±standard deviation). Immunization with AIC-M or AIC-H established memory spleen cells that secreted high levels of IFNγ and low levels of IL-5 in response to Amb a 1, which is indicative of a Th1 response. In contrast, immunization with unmodified Amb a 1 established memory spleen cells that secreted low levels of IFNγ and high levels of IL-5, which is indicative of a Th2 response.

Thus both AIC-M and AIC-H are able to establish a Th1 response. AIC-H produces lower antibody responses but similar cytokine responses to AIC-M.

TABLE 6

Cytokine Response to AIC-M, AIC-H, and Amb a 1

| Immunization material | IFNγ Response (pg/ml) | | IL-5 Response (pg/ml) | |
|---|---|---|---|---|
| | Amb a 1 Stimulation | Media Control | Amb a 1 Stimulation | Media Control |
| AIC-M Lot BK12 | 40039 ± 28924 | 1038 ± 1329 | 65 ± 60 | <32 ± 0 |
| AIC-H Lot BK8 | 37572 ± 23743 | 766 ± 962 | 38 ± 12 | <32 ± 0 |
| Amb a 1 Lot 12 April 98 | 1515 ± 1525 | 915 ± 1095 | 466 ± 5770 | <32 ± 0 |

The data shown in Table 7 (mean titer±standard deviation) depict the induction of IFN-γ (Th1 cytokine) production when mice were immunized with AIC-M and two different lots of AIC-H. In contrast, immunization with Amb a I produced little IFN-γ. Little or no IL-5 (Th2 cytokine) production was observed when mice were immunized with AIC-M and AIC-H. Amb a I immunization induced high levels of IL-5 production. These data show that immunization of mice with AIC-M and AIC-H is effective at shifting the cytokine profile to reflect a strong Th1-type bias.

TABLE 7

Cytokine Response to AIC-M, AIC-H, and Amb a 1

| Immunization material | IFNγ Response (pg/ml) | | IL-5 Response (pg/ml) | |
|---|---|---|---|---|
| | Amb a 1 Stimulation | Media Control | Amb a 1 Stimulation | Media Control |
| AIC-M Lot BK10 | 24539 ± 27704 | 203 ± 241 | 37 ± 10 | <32 ± 0 |
| AIC-H Lot BK8 | 12030 ± 12983 | 153 ± 167 | 38 ± 20 | <32 ± 0 |
| AIC-H Lot BK27 | 34772 ± 25803 | 233 ± 164 | 43 ± 14 | <32 ± 0 |
| Amb a 1 Lot 12 April 98 | 1980 ± 1215 | 230 ± 260 | 3049 ± 2644 | <34 ± 7 |

FIGS. 5, 6, 8, 9 and 15 depict IL-5 and IFN-γ production in response to AIC-L, AIC-M, AIC-H and Amb a 1 administration. These data indicate that AIC-L, AIC-M, AIC-H are effective inducing a Th1-type cytokine profile.

Example 4

Th1-Associated Cytokines Induced in Human Cells of with AIC-H and AIC-M

In this assay, peripheral blood mononuclear cells (PBMCs) were prepared from blood of ragweed-allergic human subjects. These cells were cultured at $2 \times 10^6$/ml with 5 μg/ml of Amb a 1, AIC-M or AIC-H for 6 days. Supernatants were harvested and the IFN-γ content of the supernatant was measured by ELISA. Some cells were restimulated on day 6 with 2.5 μg/ml phytohemagglutinin (PHA) and 10 ng/ml phorbol 12-myristate 13-acetate (PMA) for 24 hours, after which supernatants were harvested and the IL-4 and IL-5 content of the supernatants were measured by ELISA. Cytokine responses of the PBMCs from ragweed allergic subjects are shown in Table 8 (mean±standard deviation). Both AIC-H and AIC-M are able to stimulate a Th1-type cytokine response in cells from individuals allergic to ragweed. In contrast, Amb a 1 produced a Th2-type The different immunomodulatory properties that AIC-L, AIC-M and AIC-H conjugates display in immunized mice are summarized in Table 9. These data demonstrate that the ISS-conjugates differ from Amb a I (antigen alone) by their ability to bias immune response towards Th1-type response. Further, the ISS-conjugates have unique properties that distinguishes them from each other. AIC-L induces high antibody production, a moderate shift towards Th 1 polarity and moderate suppression of histamine release. In contrast, AIC-M induces slightly lower antibody production, strong production of IFN-γ, strong shift towards Th1 polarity early after immunization, and even stronger suppression of histamine release. Yet further in contrast, AIC-H induces low antibody production, the highest production of IFN-γ of these three compositions, a strong shift towards Th1 polarity late after immunization, and the strongest suppression of histamine release.

Example 6. AIC-Conjugate Populations Induce CTL Activity

Antigen-ISS conjugates of differing classes were tested for the ability to induce cytotoxic T lymphocyte (CTL) activity in mice.

OIC-L ISS, OIC-M ISS, and OIC-H ISS are conjugates of the antigen ovalbumin (OVA) and the ISS-containing polynucleotide SEQ ID NO:1. OIC-M control A is a covalent conjugate of OVA and non-ISS polynucleotide 5'-TGACTGTGAAGGTTAGAGATGA-3' (SEQ ID NO:9). OIC-M control B is a covalent conjugate of OVA and non-ISS polynucleotide 5'-TGACTGTGAACCTTAGAGATGA-3' (SEQ ID NO:10). These conjugates were prepared essentially as described in Example 1.

Mice were immunized twice (at a two week interval) intradermally with 10 μg of OVA conjugate or OVA antigen alone. At 4 weeks post second immunization, spleens were harvested and assayed for OVA-specific cytotoxic T lymphocyte activity. Briefly, spleens were dissociated through a

TABLE 10

Summary of immunomodulatory effects induced by AIC-L, AIC-M, AIC-H, or Amb a I

| Antigen | Lots | Antibody titers | Cytokine production | Ratio of Th1 to Th2 antibodies | | Th1 response | Th2 response | Suppression of histamine release |
|---|---|---|---|---|---|---|---|---|
| | | | | 1st imm. | 2nd imm. | | | |
| AIC-L (1 μg) | BK11 | ++++ | N.D. | 4.3 ± 2.9 | 1.4 ± 0.3 | ++ | − | 62-fold less than Amb a I |
| AIC-M (1 μg) | BK10 BK12 | +++ | IFN-γ +++ IL-5 ± | 10.7 ± 1.8 | 2.5 ± 1.8 | +++ | − | ~100-fold less than Amb a I |
| AIC-H (1 μg) | BK8 BK27 | + | IFN-γ ++++ IL-5 ± | 2.5 ± 1.8 | 7.5 ± 1.8 | +++ | − | >1000-fold less than Amb a I |
| Amb a I (10 μg) | Apr. 12, 1998 Jul. 11, 1998 Aug. 3, 1998 | ++ | IFN-γ ± IL-5 ++++ | 0.1 ± 0.2 | 0.01 ± 0.007 | − | +++ | — |

Table 11 is a summary of the ratio of Amb a 1-specific Th1 antibodies to Th2 antibodies generated in response to the conjugates at different time points in several experiments.

TABLE 11

| Conjugate (lot #) | Ratio of IgG2a to IgG1 after 1st immunization | Ratio of IgG2a to IgG1 after 2nd immunization |
|---|---|---|
| AIC-L (Lot BK11) | 4.65 | 1.66 |
| | 6.97 | 1.2 |
| | 1.2 | |
| average response | 4.27 | 1.43 |
| standard deviation | 2.9 | 0.32 |
| range | 1.37–7.17 | 1.11–1.75 |
| AIC-M (Lot BK10) | 9.5 | |
| | 15.42 | 5.78 |
| | 15.34 | 2.97 |
| (Lot BK12) | 9.42 | 2.53 |
| | 12 | |
| average response | 10.71 | 2.53 |
| standard deviation | 1.82 | 1.76 |
| range | 8.89–12.53 | 0.77–4.29 |
| AIC-H (Lot BK8) | 2.75 | 11.44 |
| | 4.3 | 5.1 |
| | 0.65 | 5.91 |
| average response | 2.57 | 7.48 |
| standard deviation | 1.83 | 3.45 |
| range | 0.73–4.39 | 4.03–10.93 | wire screen, resuspended in cell 1=culture media and counted. A portion of the cells from each spleen was treated to act as antigen presenting cells (APCs) with a peptide specific for the OVA CTL epitope (SIINFEKL, SEQ ID NO:11) recognized by H-2b mice. These cells were incubated with peptide (1 μg/ml) for 1 hour at 37° C. with 7% $CO_2$ and then washed and plated into 24-well flat bottom tissue culture plates at a concentration of $1 \times 10^6$ cells/well. Each well also received an additional $4 \times 10^6$ untreated spleen cells/well (for a total of $5 \times 10^6$ cells/well). Cell culture media for plating was supplemented with Rat T-Stim as a source of IL-2, and these effector cells were incubated at 37° C. with 7% $CO_2$ for 7 days. Cells were fed on Day 3 and washed and replated on Day 5. On Day 7, EL-4 target cells were peptide pulsed (with the SIINFEKL (SEQ ID NO:11) peptide) and washed. The Day 7 effector cells were counted and plated with target cells to achieve various effector:target ratios (40:1, 10:1, 2.5:1) and incubated at 37° C. with 7% $CO_2$ for 4 hours. Supernatant from each well was collected and assayed for lactate dehydrogenase (LDH) as a measure of cell killing, and % lysis was calculated.

Figure 16:
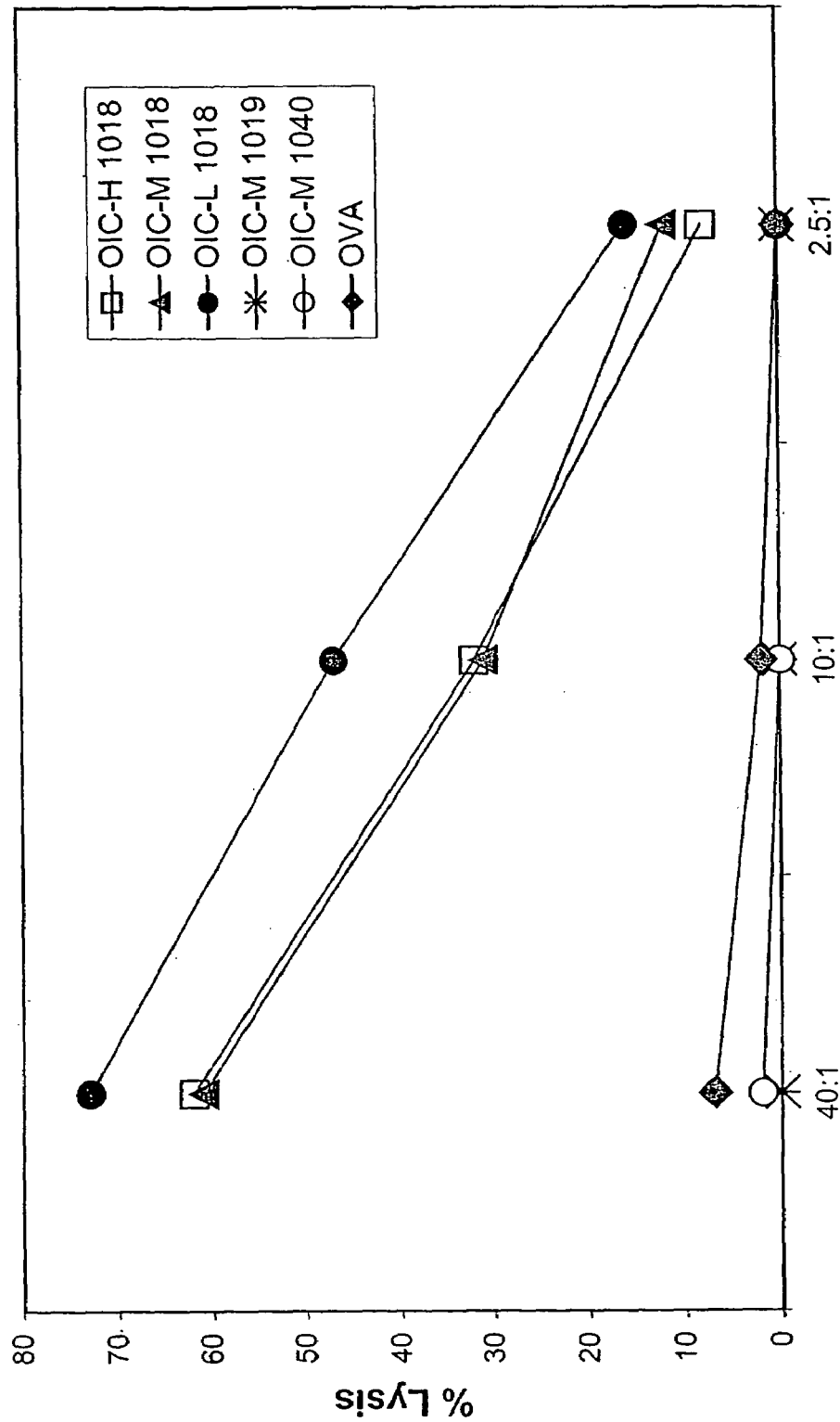
FIG. 16 is a graph depicting antigen-specific CTL responses from mice receiving various conjugate classes compared to receiving antigen alone, ovalbumin (OVA, solid diamond). Results are depicted from the following conjugates: OIC-H ISS (open square), OIC-M ISS (solid triangle), OIC-L ISS (solid circle), OIC-M control A (X), OIC-M control B (open circle).

CTL results from such an experiment are depicted in FIG. 16. Antigen-ISS conjugates of all classes (H, M and L) induced greater CTL activity in mice than antigen alone or than antigen conjugated with non-ISS polynucleotides.

Example 7

AIC-Conjugate Populations Exhibit Differing Extents of Ability to Compete with Antigen-Specific Antibody for Binding to Antigen A competition ELISA was performed to compare the ability of different Amb a 1 conjugate populations to compete with Amb a 1 specific IgE to bind to Amb a 1.

Ninety-six well plates were coated with Amb a 1 at 1.0 μg/ml in coating buffer (0.1 M $Na_2PHO_4$, pH 9.0), 100 μl/well overnight at 4° C. Plates were washed 6 times with wash buffer (1×PBS/0.05% Tween 20), using a plate washer. Two hundred μl of blocking buffer was added and plates were incubated about 1 hour or more at room temperature. Plates were then washed six times with wash buffer. Serial dilutions of Amb a 1 and conjugate were prepared in 96 well plates. The following was added to antigen coated plates: (a) 100 μl dilution buffer to all blank wells; (b) 100 μl of each sample, pre-incubated with Amb a 1 or conjugate and serum, in duplicate to appropriate wells. Plates were incubated for 30 minutes at room temperature, followed by washing 6 times with wash buffer. For antibody detection, 100 μl/well of goat anti-human IgE-biotin conjugated antibody was added at 1:50 dilution buffer to all wells, followed by incubations at room temperature for 1 hour. Plates were washed 6 times in whas buffer. One hundred μl/well of streptavidin-horseradish peroxidase (HRP) (at 1:50,000 in dilution buffer) was added to all wells, followed by incubation at room temperature for one hour. Plates were washed six times in wash buffer and developed. In this experiment, development time was approximately 22 minutes. Plates were read at 450 nm with subtraction at 650 nm (Emax with SOFTmax Pro (software version 2.6.1, Molecular Devices). For Amb a 1, AIC-M, and AIC-H, ng/ml at 50% inhibition was 40, 120, and 190, respectively (two lots of AIC-H were tested and gave the same value). The ratio of AIC-M to Amb a I for 50% inhibition was 3. The ratio of AIC-H to Amb a 1 for 50% inhibition was 4.75.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

We claim:

1. A population of conjugate molecules, said conjugate molecules comprising an allergen and a polynucleotide comprising an immunostimulatory sequence (ISS), wherein said ISS comprises a 5'-cytosine guanine-3' dinucleotide, wherein the polynucleotide is greater than 8 and less than about 200 nucleotides in length and wherein the extent of conjugation in the population provides an average of at least 5.5 ISS-containing polynucleotides per allergen molecule.

2. The population of claim 1, wherein said immunostimulatory sequence comprises the sequence 5'-T, C, G-3'.

3. The population of claim 1, wherein said immunostimulatory sequence comprises the sequence 5'-purine, purine, C, G, pyrimidine, pyrimidine-3'.

4. The population of claim 3, wherein said immunostimulatory sequence comprises a sequence selected from the group consisting of GACGCT, GACGTC, GACGTT, GACGCC, GACGCU, GACGUC, GACGUU, GACGUT, GACGTU, AGCGTT, AGCGCT, AGCGTC, AGCGCC, AGCGUU, AGCGCU, AGCGUC, AGCGUT, AGCGTU, AACGTC, AACGCC, AACGTT, AACGCT, AACGUC, AACGUU, AACGCU, AACGUT, AACGTU, GGCGTT, GGCGCT, GGCGTC, GGCGCC, GGCGUU, GGCGCU, GGCGUC, GGCGUT, and GGCGTU.

5. The population of claim 3, wherein said immunostimulatory sequence comprises the sequence 5'-purine, purine, C, G, pyrimidine, pyrimidine, C, C-3'.

6. The population of claim 5, wherein said immunostimulatory sequence comprises a sequence selected from the group consisting of GACGCTCC, GACGTCCC, GACGTTCC, GACGCCCC, AGCGTTCC, AGCGCTCC, AGCGTCCC, AGCGCCCC, AACGTCCC, AACGCCCC, AACGTTCC, AACGCTCC, GGCGTTCC, GGCGCTCC, GGCGTCCC, and GGCGCCCC.

7. The population of claim 6, wherein said immunostimulatory sequence comprises a sequence selected from the group consisting of 5'-TCATCTCGAACGTTCCA-CAGTCA-3' (SEQ ID NO:3), 5'-TGACTGTGAACGTTC-CAGATGA-3' (SEQ ID NO:4), and 5'-TGACTGTGAAB-GTTCCAGATGA-3' (SEQ ID NO:6) where B is 5-bromocytosine.

8. The population of claim 1, wherein said ISS comprises the sequence 5'-purine, purine, C, G, pyrimidine, pyrimidine, C, G-3'.

9. The population of claim 8, wherein said ISS comprises a sequence selected from the group consisting of GACGCTCG, GACGTCCG, GACGCCCG, GACGTTCG, AGCGCTCG, AGCGTTCG, AGCGTCCG, AGCGCCCG, AACGTCCG, AACGCCCG, AACGTTCG, AACGCTCG, GGCGTTCG, GGCGCTCG, GGCGTCCG, and GGCGC-CCG.

10. The population of claim 9, wherein said immunostimulatory sequence comprises a sequence selected from the group consisting of 5'-TGACTGTGAACGTTC-GAGATGA-3' (SEQ ID NO:1), 5'-TGACCGTGAACGT-TCGAGATGA-3' (SEQ ID NO:2), 5'-TCCATAACGT-TCGCCTAACGTTCGTC-3' (SEQ ID NO:5) 5'-TGACTGTGAABGTTCGAGATGA-3' (SEQ ID NO:7) where B is 5-bromocytosine, and 5'-TGACTGTGAABGTT-BGAGATGA-3' (SEQ ID NO:8) where B is 5-bromocytosine.

11. A composition comprising the population of claim 1 in a pharmaceutically acceptable excipient.

12. A population of conjugate molecules, said conjugate molecules comprising an allergen and a polynucleotide comprising an immunostimulatory sequence (ISS), wherein said ISS comprises a 5'-cytosine guanine-3' dinucleotide, wherein the polynucleotide is greater than 8 and less than about 200 nucleotides in length and wherein the extent of conjugation in the population provides a ratio of (i) average mass of ISS-containing polynucleotide to (ii) average mass of allergen of at least about 45 to about 40.

13. The population of claim 12, wherein said immunostimulatory sequence comprises the sequence 5'-T, C, G-3'.

14. The population of claim 12, wherein said immunostimulatory sequence comprises the sequence 5'-purine, purine, C, G, pyrimidine, pyrimidine-3'.

15. The population of claim 14, wherein said immunostimulatory sequence comprises a sequence selected from the group consisting of GACGCT, GACGTC, GACGTT, GACGCC, GACGCU, GACGUC, GACGUU, GACGUT, GACGTU, AGCGTT, AGCGCT, AGCGTC, AGCGCC, AGCGUU, AGCGCU, AGCGUC, AGCGUT, AGCGTU, AACGTC, AACGCC, AACGTT, AACGCT, AACGUC, AACGUU, AACGCU, AACGUT, AACGTU, GGCGTT, GGCGCT, GGCGTC, GGCGCC, GGCGUU, GGCGCU, GGCGUC, GGCGUT, and GGCGTU.

16. The population of claim 14, wherein said immunostimulatory sequence comprises the sequence 5'-purine, purine, C, G, pyrimidine, pyrimidine, C, C-3'.

17. The population of claim 16, wherein said immunostimulatory sequence comprises a sequence selected from the group consisting of GACGCTCC, GACGTCCC, GACGTTCC, GACGCCCC, AGCGTTCC, AGCGCTCC, AGCGTCCC, AGCGCCCC, AACGTCCC, AACGCCCC, AACGTTCC, AACGCTCC, GGCGTTCC, GGCGCTCC, GGCGTCCC, and GGCGCCCC.

18. The population of claim 17, wherein said immunostimulatory sequence comprises a sequence selected from the group consisting of 5'-TCATCTCGAACGTTCCA-CAGTCA-3' (SEQ ID NO:3), 5'-TGACTGTGAACGTTC-CAGATGA-3' (SEQ ID NO:4), 5'-TGACTGTGAABGT-TCCAGATGA-3' (SEQ ID NO:6) where B is 5-bromocytosine.

19. The population of claim 12, wherein said ISS comprises the sequence 5'-purine, purine, C, G, pyrimidine, pyrimidine, C, G-3'.

20. The population of claim 19, wherein said ISS comprises a sequence selected from the group consisting of GACGCTCG, GACGTCCG, GACGCCCG, GACGTTCG, AGCGCTCG, AGCGTTCG, AGCGTCCG, AGCGCCCG, AACGTCCG, AACGCCCG, AACGTTCG, AACGCTCG, GGCGTTCG, GGCGCTCG, GGCGTCCG, and GGCGC-CCG.

21. The population of claim 20, wherein said immunostimulatory sequence comprises a sequence selected from the group consisting of 5'-TGACTGTGAACGTTC-GAGATGA-3' (SEQ ID NO:1), 5'-TGACCGTGAACGT-TCGAGATGA-3' (SEQ ID NO:2), 5'-TCCATAACGT-TCGCCTAACGTTCGTC-3' (SEQ ID NO:5) 5'-TGACTGTGAABGTTCGAGATGA-3' (SEQ ID NO:7) where B is 5-bromocytosine, and 5'-TGACTGTGAABGTT-BGAGATGA-3' (SEQ ID NO:8) where B is 5-bromocytosine.

22. A composition comprising the population of claim 12 in a pharmaceutically acceptable excipient.

23. The population according to claim 1, wherein the allergen is Amb a 1.

24. The population according to claim 1, wherein the allergen is selected from the group consisting of a pollen allergen, an insect allergen, a mammal allergen, a nut allergen, a crustacean allergen and a fungal allergen.

25. The population according to claim 1, wherein the allergen is selected from the group consisting of a ragweed allergen, a grass allergen, a birch allergen, a cedar allergen, a juniper allergen, a dust mite allergen, a cockroach allergen, a cat allergen, a dog allergen, a peanut allergen, a wheat allergen and a latex allergen.

26. The population according to claim 12, wherein the allergen is Amb a 1.

27. The population according to claim 12, wherein the allergen is selected from the group consisting of a pollen allergen, an insect allergen, a mammal allergen, a nut allergen, a crustacean allergen and a fungal allergen.

28. The population according to claim 12, wherein the allergen is selected from the group consisting of a ragweed allergen, a grass allergen, a birch allergen, a cedar allergen, a juniper allergen, a dust mite allergen, a cockroach allergen, a cat allergen, a dog allergen, a peanut allergen, a wheat allergen and a latex allergen.

29. The population according to claim 1, wherein the allergen is a polypeptide.

30. The population according to claim 12, wherein the allergen is a polypeptide.

31. A population of conjugate molecules made by the process comprising: combining a polynucleotide comprising an immunostimulatory sequence (ISS) and allergen at a ratio of about 17 molar equivalents of the polynucleotide to about 1 molar equivalent of the allergen whereby conjugate molecules comprising the polynucleotide and allergen are formed, wherein the polynucleotide is greater than 8 and less than about 200 nucleotides in length and wherein the ISS comprises a 5'-cytosine guanine-3' dinucleotide.

* * * * *